US012264070B2

(12) United States Patent
Ozyilmaz et al.

(10) Patent No.: US 12,264,070 B2
(45) Date of Patent: Apr. 1, 2025

(54) TWO-DIMENSIONAL AMORPHOUS CARBON COATING AND METHODS OF GROWING AND DIFFERENTIATING STEM CELLS

(71) Applicant: National University of Singapore, Singapore (SG)

(72) Inventors: Barbaros Ozyilmaz, Singapore (SG); Carlo Mendoza Orofeo, Singapore (SG); Henrik Andersen, Singapore (SG); Hongji Zhang, Singapore (SG); Chee Tat Toh, Singapore (SG); Inigo Martin-Fernandez, Singapore (SG)

(73) Assignee: National University of Singapore, Singapore (SG)

( * ) Notice: Subject to any disclaimer, the term of this patent is extended or adjusted under 35 U.S.C. 154(b) by 1195 days.

(21) Appl. No.: 17/030,480

(22) Filed: Sep. 24, 2020

(65) Prior Publication Data
US 2021/0017026 A1 Jan. 21, 2021

Related U.S. Application Data

(62) Division of application No. 15/901,099, filed on Feb. 21, 2018, now Pat. No. 11,192,788.
(Continued)

(51) Int. Cl.
*C01B 32/05* (2017.01)
*A61L 27/08* (2006.01)
(Continued)

(52) U.S. Cl.
CPC .............. *C01B 32/05* (2017.08); *A61L 27/08* (2013.01); *A61L 27/303* (2013.01); *A61L 27/50* (2013.01); *C12N 5/0602* (2013.01); *C23C 14/0005* (2013.01); *C23C 16/01* (2013.01); *C23C 16/27* (2013.01); *H01M 4/8657* (2013.01); *H01M 4/8803* (2013.01); *H01M 4/98* (2013.01); *H01M 8/1023* (2013.01); *H01M 8/1039* (2013.01);
(Continued)

(58) Field of Classification Search
None
See application file for complete search history.

(56) References Cited

U.S. PATENT DOCUMENTS

| 4,725,345 A | 2/1988 | Sakamoto et al. |
| 5,266,409 A | 11/1993 | Schmidt et al. |

(Continued)

FOREIGN PATENT DOCUMENTS

| CN | 1414644 A | 4/2003 |
| CN | 102509694 A | 6/2012 |

(Continued)

OTHER PUBLICATIONS

Adliene et al.; Materials Science and Engineering B 152; 91-95. ; 2008.*
(Continued)

*Primary Examiner* — Guinever S Gregorio
(74) *Attorney, Agent, or Firm* — Ajay A. Jagtiani; Miles & Stockbridge P.C.

(57) ABSTRACT

Described is a composite material composed of an atomically thin (single layer) amorphous carbon disposed on top of a substrate (metal, glass, oxides) and methods of growing and differentiating stem cells.

6 Claims, 17 Drawing Sheets

Related U.S. Application Data

(60) Provisional application No. 62/546,680, filed on Aug. 17, 2017, provisional application No. 62/463,112, filed on Feb. 24, 2017.

(51) Int. Cl.

| | |
|---|---|
| *A61L 27/30* | (2006.01) |
| *A61L 27/50* | (2006.01) |
| *C12N 5/071* | (2010.01) |
| *C23C 14/00* | (2006.01) |
| *C23C 16/01* | (2006.01) |
| *C23C 16/27* | (2006.01) |
| *H01M 4/86* | (2006.01) |
| *H01M 4/88* | (2006.01) |
| *H01M 4/98* | (2006.01) |
| *H01M 8/1023* | (2016.01) |
| *H01M 8/1039* | (2016.01) |
| *H01M 8/1053* | (2016.01) |
| *H01M 8/10* | (2016.01) |

(52) U.S. Cl.
CPC ....... *H01M 8/1053* (2013.01); *A61L 2420/02* (2013.01); *C01P 2002/02* (2013.01); *C01P 2002/04* (2013.01); *C01P 2002/20* (2013.01); *C01P 2006/40* (2013.01); *C12N 2501/10* (2013.01); *C12N 2533/00* (2013.01); *H01M 2008/1095* (2013.01)

(56) References Cited

U.S. PATENT DOCUMENTS

| | | | |
|---|---|---|---|
| 5,397,644 | A | 3/1995 | Yamashita |
| 5,989,672 | A | 11/1999 | Hayashi |
| 6,599,651 | B1 | 7/2003 | Saitou et al. |
| 8,569,389 | B2 | 10/2013 | Tsai et al. |
| 8,916,451 | B2 | 12/2014 | Bayram et al. |
| 8,941,950 | B2 | 1/2015 | Yuan et al. |
| 9,269,981 | B2 | 2/2016 | Iyuke et al. |
| 10,984,830 | B2 | 4/2021 | Ozyilmaz et al. |
| 11,114,674 | B2 | 9/2021 | Ozyilmaz et al. |
| 11,192,788 | B2 | 12/2021 | Ozyilmaz et al. |
| 2002/0051903 | A1 | 5/2002 | Masuko et al. |
| 2002/0155632 | A1* | 10/2002 | Yamazaki ............ H10K 71/164 118/726 |
| 2003/0082833 | A1 | 5/2003 | Yu et al. |
| 2006/0128079 | A1 | 6/2006 | Tseng et al. |
| 2007/0132375 | A1 | 6/2007 | Bachmann et al. |
| 2009/0017602 | A1 | 1/2009 | Damlencourt et al. |
| 2011/0014548 | A1 | 1/2011 | Blunk et al. |
| 2011/0020727 | A1 | 1/2011 | Burlatsky et al. |
| 2011/0048943 | A1 | 3/2011 | Nemes |
| 2011/0129675 | A1 | 6/2011 | Choi et al. |
| 2011/0151278 | A1 | 6/2011 | Gurney et al. |
| 2011/0290655 | A1 | 12/2011 | Nishikiori et al. |
| 2012/0141799 | A1 | 6/2012 | Kub et al. |
| 2013/0214875 | A1 | 8/2013 | Duncan et al. |
| 2014/0004445 | A1 | 1/2014 | Tsai et al. |
| 2014/0217356 | A1 | 8/2014 | Bayram et al. |
| 2014/0248513 | A1 | 9/2014 | Takizawa et al. |
| 2014/0356764 | A1 | 12/2014 | Iseki et al. |
| 2016/0111180 | A1* | 4/2016 | Joo .................... H01L 29/66742 73/31.06 |
| 2017/0032815 | A1 | 2/2017 | Oezyilmaz et al. |
| 2017/0047223 | A1 | 2/2017 | Wang et al. |
| 2017/0186457 | A1 | 6/2017 | Ng et al. |
| 2018/0323461 | A1 | 11/2018 | Suzuki et al. |
| 2018/0337411 | A1 | 11/2018 | Ozyilmaz et al. |
| 2019/0080713 | A1 | 3/2019 | Ozyilmaz et al. |
| 2019/0088420 | A1 | 3/2019 | Tour et al. |
| 2021/0017026 | A1 | 1/2021 | Ozyilmaz et al. |

FOREIGN PATENT DOCUMENTS

| | | |
|---|---|---|
| CN | 102576890 A | 7/2012 |
| CN | 104080945 A | 10/2014 |
| CN | 104278241 A | 1/2015 |
| CN | 106061893 A | 10/2016 |
| CN | 107003275 A | 8/2017 |
| CN | 109534315 A | 3/2019 |
| DE | 102009034573 A1 | 2/2010 |
| EP | 2 811 049 A1 | 12/2014 |
| JP | 09091686 A | 9/1995 |
| JP | 2002143185 A | 5/2002 |
| JP | 02002312923 A | 10/2002 |
| JP | 2005-203216 A | 7/2005 |
| JP | 2005-523050 A | 8/2005 |
| JP | 2007-265916 A | 10/2007 |
| JP | 2011-142082 A | 7/2011 |
| JP | 2011-148686 A | 8/2011 |
| JP | 2014-004166 A | 1/2014 |
| JP | 2019-10013 A | 1/2016 |
| KR | 2002-0048531 A | 6/2002 |
| KR | 10-2009-0012304 A | 2/2009 |
| KR | 2016-0044977 A | 4/2016 |
| KR | 10-2360025 B1 | 2/2022 |
| KR | 10-2450915 B1 | 9/2022 |
| WO | 02/09242 A2 | 1/2002 |
| WO | 03/065881 A2 | 8/2003 |
| WO | 2016/042309 A1 | 3/2016 |
| WO | 2018/156082 A1 | 8/2018 |
| WO | 2020/027728 A1 | 2/2020 |
| WO | 2021/054900 A1 | 3/2021 |

OTHER PUBLICATIONS

Office Action and Search Report received in Chinese Application No. 202180033843.X dated Dec. 18, 2023.
Office Action received in U.S. Appl. No. 16/181,656 mailed Dec. 3, 2020.
Extended European Search Report received in European Application No. 18757600.4 mailed Nov. 19, 2020.
International Preliminary Report on Patentability received in International Application No. PCT/SG2018/050082 issued Aug. 27, 2019.
International Search Report received in International Application No. PCT/SG2018/050082 mailed May 14, 2018.
Casiraghi et al., "Dynamic Roughening of Tetrahedral Amorphous Carbon", Physical Review Letters, vol. 91, No. 22, pp. 226104-1-226104-4 (2003).
D'Angelo et al., "Micropatterned Hydrogenated Amorphous Carbon Guides Mesenchymal Stem Cells Towards Neuronal Differentiation", European Cells and Materials, vol. 20, pp. 231-244 (2010).
Mattioli et al., "Nanostructured Polystyrene Films Engineered by Plasma Processes: Surface Characterization and Stem Cell Interaction", Journal of Applied Polymer Science, pp. 40427 (1-10) (2014).
Joo et al., "Realization of continuous Zachariasen carbon monolayer", Science Advances, vol. 3, pp. 1-8 (2017).
Kotakoski et al., "From Point Defects in Graphene to Two-Dimensional Amorphous Carbon", Physical Review Letters, vol. 106, No. 10, pp. 105505-1-105505-4 (2011).
Suk et al., Mechanical measurements of ultra-thin amorphous carbon membranes using scanning atomic force microscopy, Carbon, vol. 50, No. 6, pp. 2220-2225 (2012).
Office Action received in Japanese Application No. 2019-546155 mailed Nov. 17, 2020.
Office Action received in U.S. Appl. No. 15/901,099 mailed Apr. 1, 2020.
Office Action received in U.S. Appl. No. 16/049,034 mailed Mar. 31, 2020.
Kotakoski et al., "Toward Two-Dimensional All-Caron Heterostructures via Ion Beam Patterning of Single-Layer Graphene", Nano Letters, vol. 15, pp. 5944-5949 (2015).
Zhao et al., "Sythesis of large-scale undoped and nitrogen-doped amorphous graphene on MgO substrate by chemical vapor deposition", Journal of Materials Chemistry, vol. 22, pp. 19679-19683 (2012).

(56) References Cited

OTHER PUBLICATIONS

Office Action received in Chinese Application No. 201980050734.1 dated Mar. 30, 2022.
Ran et al., "Fabrication and Structure Characterization of Quasi-2-Dimensional Amorphous Carbon Structures", Acta Phys. Chim. Sin. 28 (7), pp. 1551-1555 (2012).
Kotakoski et al., "From Point Defects in Graphene to Two-Dimensional Amorphous Carbon", Physical Review Letters, PRL 106, pp. 105505-1 to 105505-4 (2011).
Office Action received in Japanese Application No. 201980050734.1 issued Sep. 13, 2021.
Notice of Allowance received in Japanese Application No. 2019-546155.
Mattioli et al., "Nanostructered Polystyrene Films Engineered by Plasma Processes: Surface Characterization and Stem Cell Interaction", Journal Applied Polymer Science, Wiley Periodicals Inc., vol. 131, pp. 40427 (1-10), (2014).
Mattioli et al., "Nanostructured Polystyrene Films Engineered by Plasma Processes: Surface Characterization and Stem Cell Interaction", Journal of Applied Polymer Science, Wiley Periodicals, Inc., vol. 131, pp. 40427 (1-10); (2014).
Official Action received in Japanese Application No. 2021-505189 dated Sep. 16, 2022.
Action received in Korean Application No. 10-2019-7027503 dated Nov. 11, 2022.
Action received in Korean Application No. 10-2021-7001792 dated Oct. 31, 2022.
Office Action received in Chinese Application No. 201880013364.X issued Sep. 14, 2023.
Office Action received in Japanese Application No. 2022-117400 issued Sep. 12, 2023.
Mattioli et al., "Nanostructured Polystyrene Films Engineered by Plasma Processes: Surface Characterization and Stem Cell Interaction", Journal of Applied Polymer Science, DOI: 10.1002/app. 40427 (2014).
Ran et al., "Fabrication and Structure Characterization of Quasi-2-Dimensional Amorphous Carbon Structures", Acta Physico-Chimica Sinica vol. 28, No. 7, pp. 1551-1555 (2012).
Notification of Re-examination received in Chinese Application No. 201980050734.1 mailed Nov. 27, 2023.
Decision of Final Rejection received in Chinese Application No. 201980050734.1 issued Jan. 5, 2023.
Office Action received in U.S. Appl. No. 15/901,099 mailed Jan. 13, 2021.
Ferrari, A.C. et al. "Interpretation of Raman spectra of disordered and amorphous carbon." Physical Review B 61, 14095-14107 (2000).
Robertson, J. "Ultrathin carbon coatings for magnetic storage technology." Thin Solid Films 383, 81-88 (2001).
Hu, S. et al. "Proton transport through one-atom-thick crystals." Nature 516, 227-230 (2014).
Das, S. et al. "Measurements of adhesion energy of graphene to metallic substrates." Carbon 59, 121-129 (2013).
Schriver, M. et al. "Graphene as a Long-Term Metal Oxidation Barrier: Worse Than Nothing" ACS Nano 7, 5763-5768 (2013).
Wang, J. S. et al. "The mechanical performance of DLC films on steel substrates." Thin Solid Films 325, 163-174 (1998).
Leng, Y. X. et al. "Mechanical properties and platelet adhesion behavior of diamond-like carbon films synthesized by pulsed vacuum arc plasma deposition." Surface Science 531, 177-184 (2003).
Maguire, P. D. et al. "Mechanical stability, corrosion performance and bioresponse of amorphous diamond-like carbon for medical stents and guidewires." Diamond and Related Materials 14, 1277-1288 (2005).
Marcon, et al. "The head-disk interface roadmap to an areal density of 4 Tbit/in2." Advances in Tribology 2013, 1-8 (2013).
Discher, D. E., Mooney, D. J. & Zandstra, P. W. "Growth Factors, Matrices, and Forces Combine and Control Stem Cells." Science 324, 1673-1677 (2009).
Spradling, A., Drummond-Barbosa, D. & Kai, T. "Stem cells find their niche." Nature 414, 98-104 (2001).
Murry, C. E. & Keller, G. "Differentiation of Embryonic Stem Cells to Clinically Relevant Populations: Lessons from Embryonic Development." Cell 132, 661-680 (2008).
Engler, A. J., Sen, S., Sweeney, H. L. & Discher, D. E. "Matrix Elasticity Directs Stem Cell Lineage Specification." Cell 126, 677-689 (2006).
Dalby, M. J. et al. "The control of human mesenchymal cell differentiation using nanoscale symmetry and disorder." Nature Materials 6, 997-1003 (2007).
Trappmann, B. et al. "Extracellular-matrix tethering regulates stem-cell fate." Nature Materials 11, 642-649 (2012).
Lee, H. et al. "Establishment of feeder-free culture system for human induced pluripotent stem cell on DAS hanocrystalline graphene." Scientific Reports 6, 20708 (2016).
Choi, W. J. et al. "Effects of substrate conductivity on cell morphogenesis and proliferation using tailored, atomic layer deposition-grown ZnO thin films." Scientific Reports 5, 9974 (2015).
Huang et al.; Synthesis of Large-Scale Undoped and Nitrogen-Doped Amorphous graphene on MgO Substrate by Chemical Vapor Deposition; J. Mater. Chem., 22, 19679; 2012.
Chae et al., "Mass Transport through a Proton Exchange Membrane (Nafion) in Microbial Fuel Cells", Energy & Fuels, 22, pp. 169-176 (2008).
Office Action received in U.S. Appl. No. 15/901,099 mailed Aug. 19, 2020.
Office Action received in U.S. Appl. No. 16/049,034 mailed Aug. 21, 2020.
Office Action received in U.S. Appl. No. 16/181,656 mailed Aug. 19, 2020.
Dwivedi et al., "Understanding the Role of Nitrogen in Plasma-Assisted Surface Modification of Magnetic Recording Media with and without Ultrathin Carbon Overcoats", Scientific Reports, vol. 5; No. 7772; pp. 1-13 (2015).
Pathem et al., Carbon Overcoat Oxidation in Heat-Assisted Magnetic Recording; IEEE Transactions on Magentics; vol. 49; No. 7; pp. 3721-3724 (2013).
International Search Report and Written Opinion received in International Application No. PCT/SG2019/050374 mailed Oct. 3, 2019.
Choi et al., "Effects of substrate conductivity on cell morphogenesis and proliferation using tailored, atomic layer deposition-grown ZnO thin films", Scientific Reports, vol. 5, 9974 pp. 1-9 (2015).
Japanese Office Action received in Japanese Patent Application No. 2021-166403 mailed Jan. 18, 2022.
Office Action received in Japanese Application No. 2019-546155 mailed Jun. 8, 2021.
Notification of Fulfilling of Registration Formality (Notice of Grant of Patent) received in Chinese Application No. 201980050734.1 dated May 1, 2024.
Extended European Search Report received in European Application No. 18757600.4 dated Nov. 19, 2020.
Notice of Reasons for Refusal received in Japanese Application No. 2019-546155 dated Nov. 17, 2020.
Decision to Grant a Patent received in Japanese Application No. 2021-166403 dated Jun. 4, 2022.
Decision to Grant a Patent received in Japanese Application No. 2022-117400 dated May 7, 2024.
Notice of Allowance received in Korean Application No. 10-2019-7027503 dated Jul. 26, 2023.
Notice for Eligibility of Grant received in Singapore Application No. 11201907148S dated Dec. 7, 2023.
Third Office Action received in Chinese Application No. 201980050734.1 dated Jun. 22, 2022.
Patent Decision received in Korean Application No. 10-2021-7001792 dated May 22, 2023.
Notice of Reasons for Refusal received in Japanese Application No. 2022-554483 dated Nov. 1, 2024.
Office Action received in U.S. Application No. 17/910, 180 dated Jan. 18, 2024.
Luo et al., "Influence of Source and Drain Contacts on the Properties of Indium-Gallium-Zinc-Oxide Thin-Film Transistors based

(56) References Cited

OTHER PUBLICATIONS on Amorphous Carbon Nanofilm as Barrier Layer", Applied Materials and Interfaces, vol. 7, pp. 3633-3640 (2015).
Notification of Transmittal and International Search Report and Written Opinion received in PCT Application No. PCT/SG2021/050118 dated May 28, 2021.
Zheng et al., "Interconnected hollow carbon nonospheres for stable lithium metal anodes", Nature Nanotechnology, vol. 9, pp. 618-623 (2014).
First Office Action received in Chinese Application No. 202180033843.X dated Dec. 18, 2023.
Joo et al., "Realization of continuous Zachariasen carbon monlayer", Science Advances, vol. 3, pp. 1-8 (2017).
Written Opinion received in Singapore Application No. 11202252887H dated Sep. 13, 2024.
Toh et al., "Synthesis and properties of free-standing monolayer amorphous carbon", Nature, vol. 577, pp. 199-115 (2020).
Final Office Action received in U.S. Appl. No. 17/910,180 Aug. 14, 2024.
Toh et al., "Synthesis and properties of free-standing monolayer amorphous carbon", Nature; vol. 577; pp. 199-203 (2002).
Joo et al., "Realization of continuous Zachariasen carbon monolayer", Science Advances; vol. 3; pp. e1601821:1-e1601821:8 (2017).
Li et al., "The van der Waals epitaxy of Bi2Se3 on the vicinal Si(111) surface: an approach for preparing high-quality thin films of a topological insulator", New Journal of Physics; vol. 12, 103038 (11 pp) (2010).
European Search Report received in European Application No. 21768280.6 dated Apr. 3, 2024.
Non-Final Office Action received in U.S. Appl. No. 17/910,180 dated Apr. 10, 2024.
International Search Report and Written Opinion received in PCT Application No. PCT/SG2021/050118 dated May 28, 2021.
Felix et al., "On the Mechanical Properties and Thermal Stability of a Recently Synthesized Monolayer Amorphous Carbon", The Journal of Physical Chemistry, vol. 124, pp. 14855-14860 (2020).
Second Office Action received in Chinese Application No. 201880013364.X issued Mar. 20, 2024.

\* cited by examiner

TWO-DIMENSIONAL AMORPHOUS CARBON COATING AND METHODS OF GROWING AND DIFFERENTIATING STEM CELLS

CROSS-REFERENCE TO RELATED APPLICATIONS

This application is a divisional application of U.S. application Ser. No. 15/901,099 entitled, "TWO-DIMENSIONAL AMORPHOUS CARBON COATING AND METHODS OF GROWING AND DIFFERENTIATING STEM CELLS", filed Feb. 21, 2018, which claims benefit of priority of U.S. Provisional Patent Application No. 62/463,112 entitled, "LAYERED COMPOSITE MATERIAL CONSISTING ATOMICALLY THIN AMORPHOUS CARBON ON TOP OF THE SUBSTRATE," filed Feb. 24, 2017, and U.S. Provisional Patent Application No. 62/546,680 entitled, "THERAPEUTIC COATING AND METHODS OF GROWING AND DIFFERENTIATING STEM CELLS," filed Aug. 17, 2017. The entire contents and disclosures of these patent applications are incorporated herein by reference in their entirety.

BACKGROUND

Field of the Invention

The present disclosure relates to generally to two-dimensional amorphous carbon (2DAC) coating and articles and methods of growing and differentiating stem cells.

Background of the Invention

A need exists within the prior art to develop and provide suitable applications for a coating intended for specific purposes such as biomedical applications.

SUMMARY

According to first broad aspect, the present disclosure provides a two-dimensional (2D) amorphous carbon film, wherein the 2D amorphous carbon film has a crystallinity (C)≤0.8.

According to a second broad aspect, the present disclosure provides a two-dimensional (2D) amorphous carbon film, wherein the 2D amorphous carbon film has a crystallinity (C)<1 and a $sp^3/sp^2$ bond ratio is 0.2 or less.

According to a third broad aspect, the present disclosure provides an article comprising: a substrate; and a two-dimensional (2D) amorphous carbon film disposed on a surface of the substrate, wherein the 2D amorphous carbon film has a crystallinity (C)≤0.8.

According to a fourth broad aspect, the present disclosure provides a method of forming a two-dimensional (2D) amorphous carbon film, the method comprising: decomposing a precursor gas to generate at least one decomposed species; and forming the 2D amorphous carbon film from the decomposed species on a surface of the substrate, wherein the precursor gas comprises a carbon-containing gas.

According to fifth broad aspect, the present disclosure provides a two-dimensional amorphous carbon (2DAC) coating having an atomic structure consisting of non-hexagonal carbon rings, and hexagonal carbon rings, and having a ratio of the hexagonal rings to the non-hexagonal rings is less than 1.0.

According to sixth broad aspect, the present disclosure provides a method of differentiating stem cells into specialized cells, comprising: coating a surface of a substrate with two-dimensional amorphous carbon (2DAC); disposing a seed layer on the surface of the substrate coated with 2DAC; and adsorbing growth factors in a stem cell medium onto the surface of the substrate coated with 2DAC.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION

Definitions

Figure 1:
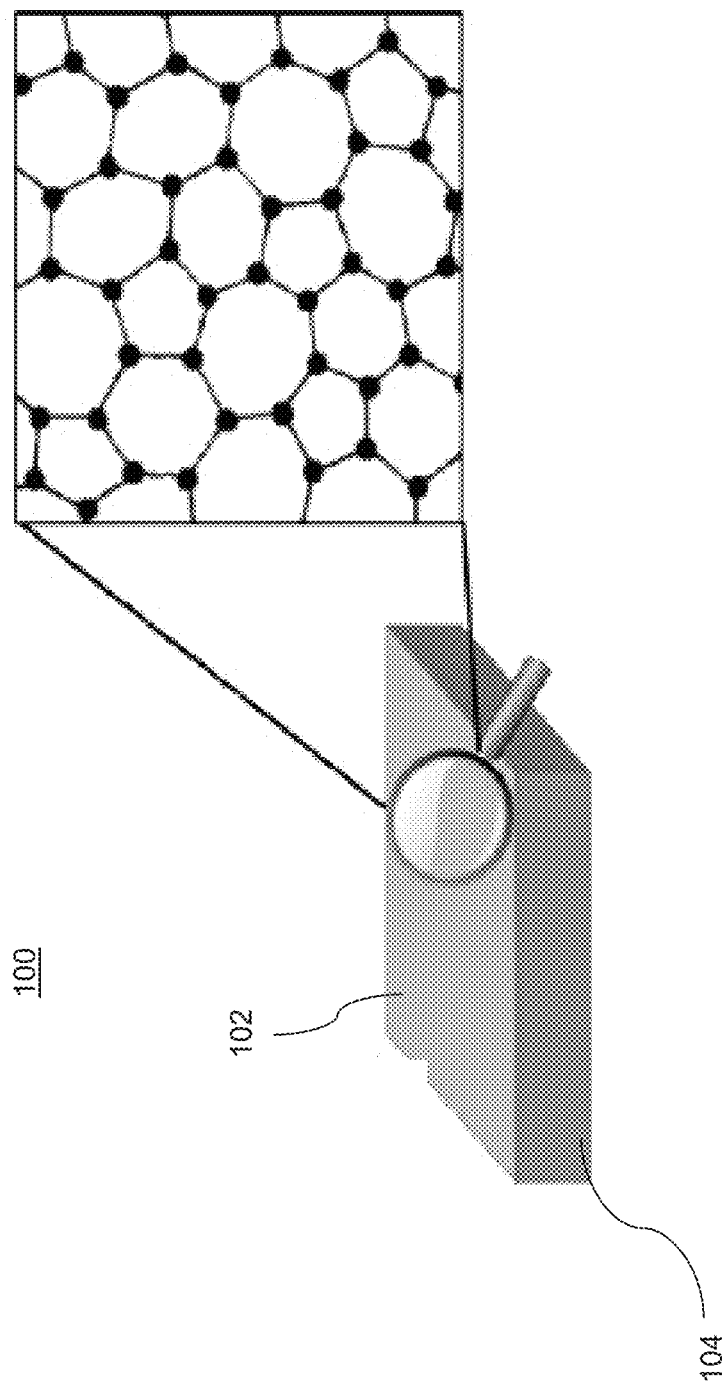
FIG. 1 is a schematic illustration showing the disclosed composite material of the atomically thin film showing random hexagon rings showing continuity and order (not graphene), according to one embodiment of the present disclosure.

Where the definition of terms departs from the commonly used meaning of the term, applicant intends to utilize the definitions provided below, unless specifically indicated.

Unless defined otherwise, all technical and scientific terms used herein have the same meaning as is commonly understood to which the claimed subject matter belongs. In the event that there is a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

For purposes of the present disclosure, the term "comprising", the term "having", the term "including," and variations of these words are intended to be open-ended and mean that there may be additional elements other than the listed elements.

For purposes of the present disclosure, directional terms such as "top," "bottom," "upper," "lower," "above," "below," "left," "right," "horizontal," "vertical," "up," "down," etc., are used merely for convenience in describing the various embodiments of the present disclosure. The embodiments of the present disclosure may be oriented in various ways. For example, the diagrams, apparatuses, etc., shown in the drawing figures may be flipped over, rotated by 90° in any direction, reversed, etc.

For purposes of the present disclosure, a value or property is "based" on a particular value, property, the satisfaction of a condition, or other factor, if that value is derived by performing a mathematical calculation or logical decision using that value, property or other factor.

For purposes of the present disclosure, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

For purposes of the present invention, the term "adhesion strength" refers to the strength of the bonding between the disclosed 2DAC film to its growth substrate. It is directly dependent on the adhesion energy between these two materials, which may be measured in $J/m^2$.

For purposes of the present invention, the term "amorphous" refers to lacking definite form or having no specific shape or being formless. As a non-crystalline solid, amorphous refers to a solid that lacks the long-range order that is characteristic of a crystal.

For purposes of the present invention, the term "amorphous carbon" refers to carbon that does not have any long range crystalline structure.

For purposes of the present invention, the term "atomically thin amorphous carbon" refers to amorphous carbon that consist of approximately one to five layers of carbon atoms in a plane, with predominantly $sp^2$ bonding between the carbon atoms and thus forming a layer. It should be appreciated that layers may be stacked, and this stacking of layers is considered within the scope of the invention.

For purposes of the present invention, the term "carbon coating" refers to a layer of carbon deposited on a substrate.

For purposes of the present invention, the term "contact angle measurement" refers to a technique to measure the hydrophobicity of a surface. In an exemplary disclosed embodiment of a water droplet, this angle may be measured from the surface to the water-air interface. A small angle means that the surface favorably attracts water and a large angle suggests that the surface repels water. This is important in the patent as certain cells favor a hydrophilic (small contact angle) surface for growth.

For purposes of the present invention, the term "diamond-like carbon" refers to amorphous carbon that consist of predominantly $sp^3$ bonding between carbon atoms.

For purposes of the present invention, the term "differentiating stem cells" refers to the process of directing an unspecialized stem cell towards a specific type of cell with functional traits. In disclosed embodiments, the differentiation occurs due to a combination of chemical and substrate induced factors.

For purposes of the present invention, the term "DIG ratio" refers to the ratio of the intensities of the D and G peak in the Raman spectrum.

For purposes of the present invention, the term "graphene" refers to an allotrope (form) of carbon consisting of a single layer of carbon atoms arranged in a hexagonal lattice. It is the basic structural element of many other allotropes of carbon, such as graphite, charcoal, carbon nanotubes and fullerenes. It can be considered as an indefinitely large aromatic molecule, the ultimate case of the family of flat polycyclic aromatic hydrocarbons. Graphene has many unusual properties including its strong materials properties, ability to efficiently conduct heat and electricity and is also nearly transparent.

For purposes of the present invention, the term "implant coating" refers to an additional layer covering the entirety or parts of the surface of a biomedical implant. An implant may also be refer to a cardiovascular stent or orthopedic implant but are not limited to these exemplary implants.

For purposes of the present invention, the term "organic light-emitting diode" (OLED) is a light-emitting diode (LED) in which the emissive electroluminescent layer is a film of organic compound that emits light in response to an electric current. This layer of organic semiconductor is situated between two electrodes; typically, at least one of these electrodes is transparent. OLEDs are used to create digital displays, for example, in devices such as television screens, computer monitors, portable systems such as mobile phones, handheld game consoles, personal digital assistants (PDAs) and handheld personal computers.

For purposes of the present invention, the term "photolytic decomposition" refers to the use of one or more photons to induce a chemical reaction of a molecule to break down into simpler particles.

For purposes of the present invention, the term "proton transport" refers to the transport of the proton across an electrically insulating membrane.

For purposes of the present invention, the term "Raman spectroscopy" refers to a spectroscopic technique used to observe vibrational, rotational, and other low-frequency modes in a system. Raman spectroscopy is commonly used in chemistry to provide a structural fingerprint by which molecules can be identified. It relies on inelastic scattering, or Raman scattering, of monochromatic light, usually from a laser in the visible, near infrared, or near ultraviolet range. The laser light interacts with molecular vibrations, phonons or other excitations in the system, resulting in the energy of the laser photons being shifted up or down. The shift in energy gives information about the vibrational modes in the system.

For purposes of the present invention, the term "Raman spectrum" refers to a phenomenon of scattering intensity as a function of frequency shifts depending on rovibronic states of a molecule. For a molecule to exhibit a Raman effect, there must be a change in its electric dipole-electric dipole polarizability with respect to the vibrational coordinate corresponding to the rovibronic state. The intensity of the Raman scattering is proportional to this polarizability change.

For purposes of the present invention, the term "ratio of $sp^a/sp^2$" refers to the type of carbon bonds found in the 2DAC. The $sp^2$ bonds allow for higher growth factor bonding.

For purposes of the present invention, the term "substrate" refers to the structural support for the disclosed two-dimensional (2D) amorphous carbon film. In select applications, disclosed embodiments provide a substrate to mechanically support, for example, the 2DAC film as, otherwise, the 2DAC film may be too thin to perform its function without getting damaged. The substrate may be regarded as the material used for growth of the disclosed 2DAC or 2DAC film on the surface of the substrate.

For purposes of the present invention, the term "thrombosis" refers to the formation of a blood clot inside a blood vessel, obstructing the flow of blood through the circulatory system.

For purposes of the present invention, the term "two-dimensional (2D) amorphous carbon film" refers to atomically thin amorphous carbon to the thinnest amorphous carbon possible (e.g., single atom thick) that can be grown directly, for example, on substrates including those having low melting temperature, are non-catalytic, and those substrates also including metal, glass and oxides surfaces. The growth on other substrates is made possible due to the low temperature at which the disclosed 2DAC film is grown. Disclosed embodiments of 2DAC film may be presented as a free-standing film or as a coating on a substrate as disclosed herein. Although the disclosed 2DAC film is amorphous, the carbon atoms bond to multiple adjacent carbon atoms in plane to form a strong network, which is very stable even when it is released from its growth substrate (free-standing). The carbon material also possesses properties for adhering to metal surfaces well, thereby ensuring full coverage across the substrate. The intrinsic thinness and the high strength of the disclosed 2DAC thin film also allow it to withstand bending of the metal substrate without breaking.

For purposes of the present invention, the term "two-dimensional (2D) amorphous carbon coating" refers to a 2DAC film directly grown and/or deposited on a substrate. Disclosed embodiments may also include the case where the 2DAC coating is transferred onto or off the substrate.

DESCRIPTION

While the invention is susceptible to various modifications and alternative forms, specific embodiment thereof has been shown by way of example in the drawings and will be described in detail below. It should be understood, however that it is not intended to limit the invention to the particular forms disclosed, but on the contrary, the invention is to cover all modifications, equivalents, and alternatives falling within the spirit and the scope of the invention.

Disclosed embodiments relate to a new composite material composed of an atomically thin (single layer) amorphous carbon on top of a substrate (metal, glass, oxides). The amorphous carbon adheres very well to the substrate upon which it is grown. Thus, the amorphous carbon material provides unique characteristics. For example, the disclosed amorphous carbon material is suitable for applications that utilize a substrate requiring a coating for a specific purpose(s). Exemplary applications may include, but not limited to, biomedical applications.

The present disclosure provides a new form of carbon referred to as two-dimensional (2D) amorphous carbon (2DAC). Disclosed embodiments provide the thinnest amorphous carbon possible (e.g., approximately single atom thick) within the 2DAC that can be grown, for instance, directly on metallic substrates including those having low melting temperature, are non-catalytic, and also including glass and oxides surfaces. In one select embodiment, having a single atom thickness is a preferred material and may establish a lower thickness limit for the 2DAC. Disclosed embodiments may include a thickness that may range up to a few atom thickness (e.g., 10 atomic thickness or about 3+nm). The disclosed 2DAC may be provided as a two-dimensional (2D) amorphous carbon film. It remains important to note, however, that as the thickness of the disclosed 2DAC increases, it remains structurally different (e.g., $sp^3$ to $sp^2$ ratio) from any other possibly existing amorphous carbon material thickness, as disclosed herein.

The growth on other substrates is made possible due to the low temperature at which the disclosed 2DAC film is grown. Although the disclosed 2DAC film is amorphous, the carbon atoms bond to multiple adjacent carbon atoms in plane to form a strong network, which is very stable even when it is released from its growth substrate (free-standing). Thus, each carbon atom is bonded to multiple carbon atoms such that there is a high density of bonds (connections). The disclosed 2DAC also possesses properties for adhering to metal surfaces well, thereby ensuring full coverage. Material properties (e.g., disclosed below), such as the intrinsic thinness and the high strength of the disclosed 2DAC thin film, also allow it to withstand bending of the metal substrate without breaking.

In accordance with disclosed embodiments, amorphous carbon may be defined as a form of carbon with no long-range structural order. It exists in several forms and, depending on its form, is often called in different names like diamond-like carbon, glassy carbon, soot, etc. Amorphous carbon may be produced by several techniques including, for example, chemical vapor deposition, sputter deposition, and cathodic arc deposition among others. In convention applications, amorphous carbon has always existed in three-dimensional form (or in bulk). The two-dimensional equivalent form of carbon is graphene; however, graphene only exists as a crystalline material (either single crystal or polycrystalline). For graphene to be synthesized, it requires high temperatures and is mostly grown on copper. As per this disclosure, disclosed embodiments have managed to create a continuous two-dimensional form of amorphous carbon that is grown at a much lower temperature and on arbitrary substrates. The composite material of the disclosed 2DAC film and substrate has characteristics that are vastly different from the bulk amorphous carbon, and even to single layer graphene.

FIG. 1 illustrates a schematic 100 of the disclosed composite materials with a TEM image of the carbon material on a top surface of a substrate. The composition of the disclosed matter is a new composite material of an atomically thin amorphous carbon 102 on top of a substrate 104 (e.g., metal or glass, oxides).

The disclosed composite material may refer to an atomically thin 2D amorphous carbon (2DAC) on top of an arbitrary substrate. In accordance with disclosed embodiments, the disclosed 2DAC film on top of the disclosed substrate may be defined in terms of its atomic structure and its properties.

Figure 2:
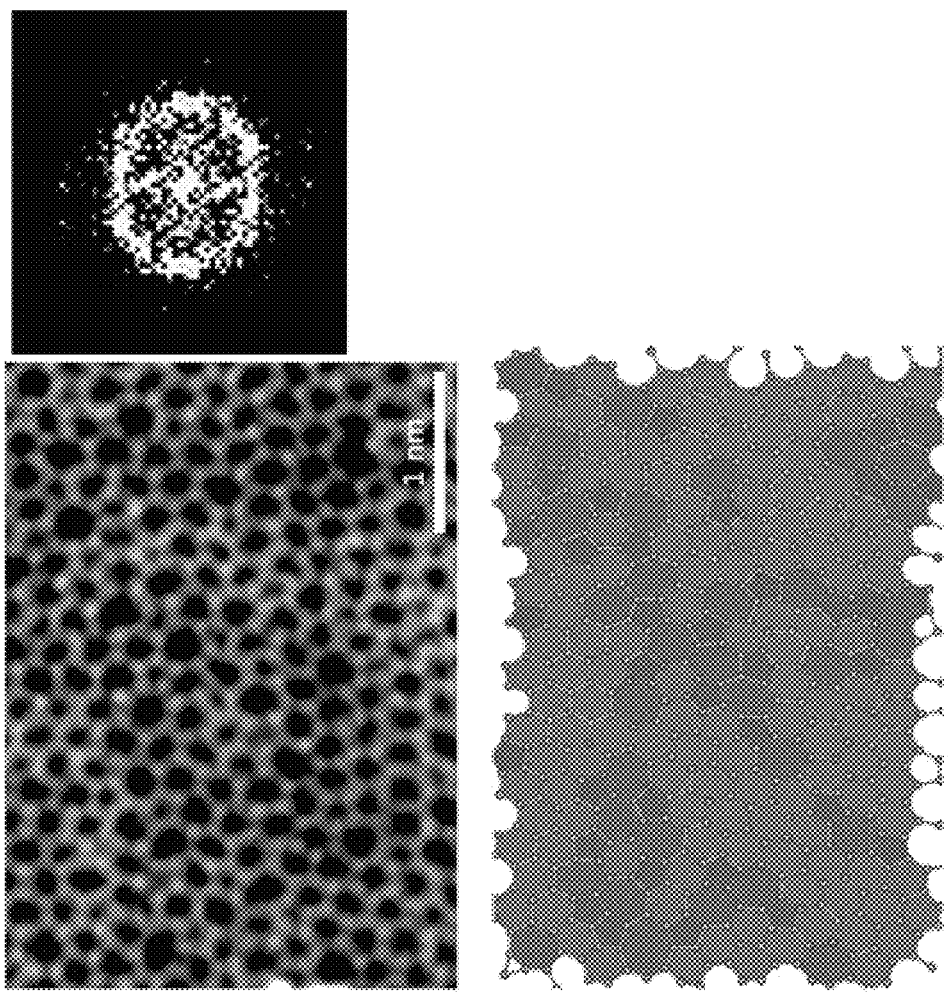
FIG. 2 illustrates a TEM image of an amorphous film showing the hexagons and non-hexagons, according to one embodiment of the present disclosure.

A closer examination and definition for the atomic structure may be presented as follows: FIG. 2 illustrates a TEM image of an amorphous film showing the hexagons and non-hexagons, according to one embodiment of the present disclosure. The upper left image of FIG. 2 illustrates a high resolution TEM image of the disclosed 2DAC film comprising hexagons and non-hexagons. A lower left schematic of the TEM image of the upper left image is provided to aid in viewing. Hexagons are colored in green, while non-hexagons are colored in either red or blue. The upper right display is an FFT illustrating which shows a ring structure with no clear diffraction patterns.

Figure 3:
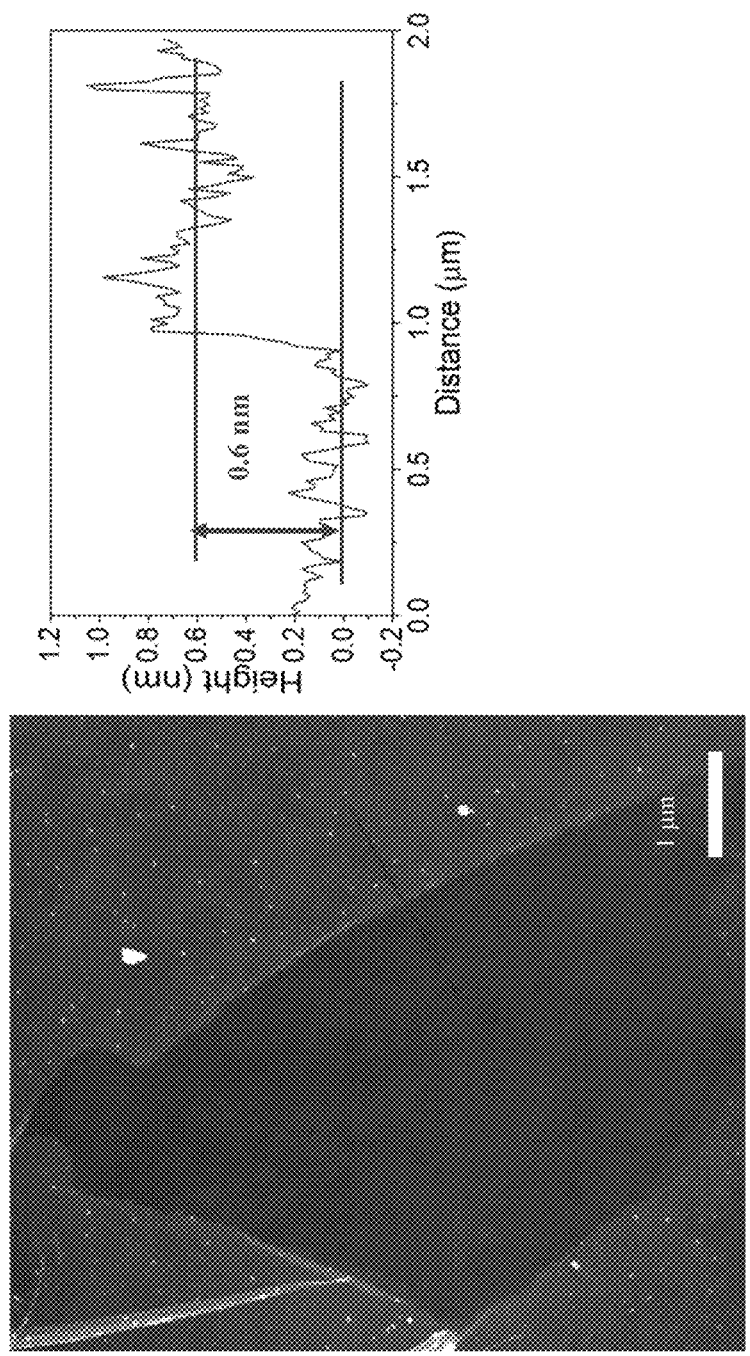
FIG. 3 illustrates a measured thickness of the disclosed carbon film on boron nitride by Atomic Force Microscopy (AFM), according to one embodiment of the present disclosure.
Figure 4:
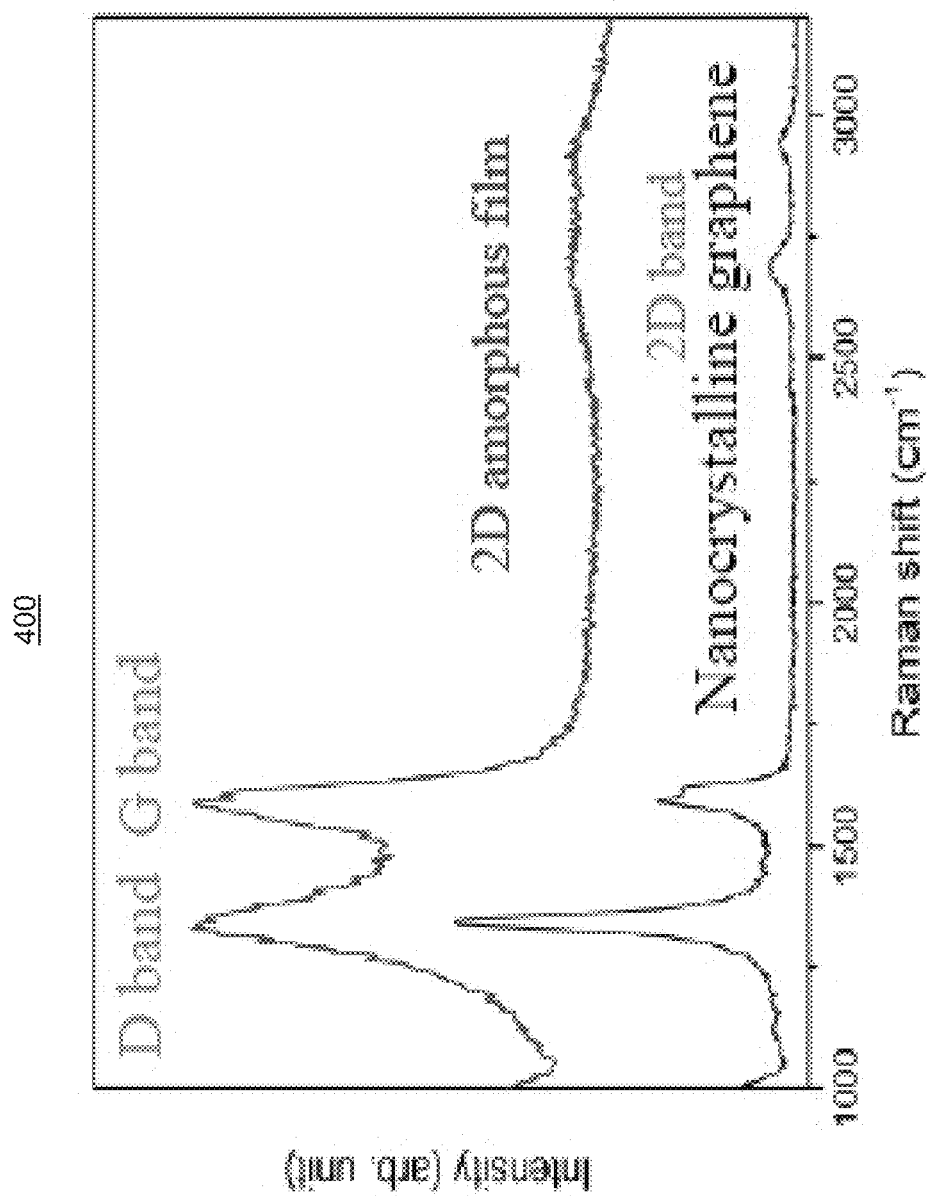
FIG. 4 illustrates a Raman spectra of amorphous film and nano-crystalline graphene on $SiO_2$, according to one embodiment of the present disclosure.

Referring to the TEM image of FIG. 2, a 2DAC film is a single-atom thick carbon film having a mixture of hexagon and non-hexagon rings in its structure. The rings are fully connected to each other, forming a network of polygons in large area film whose scale is at least in microns. The ratio of hexagons to non-hexagons is a measure of crystallinity (or amorphousity), C. Non-hexagons are in a form of 4-, 5-, 7-, 8-, 9-membered rings. A 2D amorphous film has C≤0.8, taken on a minimum imaged area of approximately 8.0 nm$^2$. The C value in FIG. 2 is approximately 0.65. Disclosed embodiments may support a C value range between and including 0.5 to 0.8. This is different from graphene where C=1 for pure hexagonal network. The non-hexagons can be randomly distributed within the hexagonal matrix, or form along the boundaries of the hexagonal domains. The domains must not be greater than 5 nm. The fast Fourier transform (FFT) of the image must not show diffraction spots (FIG. 2, upper right). The 2DAC can be released from a substrate to be free-standing or can be transferred to other substrates. Thus, in some embodiments, the disclosed 2DAC may be separating from the surface of the substrate to obtain a free-standing 2DAC film. FIG. 3 illustrates a measured thickness (i.e., the height) of the isolated disclosed 2DAC film on boron nitride (BN) by AFM. Based on the disclosed invention, the following properties apply: FIG. 3 shows the AFM of the disclosed transferred 2DAC film to boron nitride (BN). The disclosed thickness of the 2DAC is approximately 6 Å, comparable to graphene which is only one atomic thick (thickness ranges from and including 3.3 Å to 10 Å when measured on BN). The thickness is also corroborated by the TEM image in FIG. 1. Further, the film is found to be homogenous. FIG. 4 illustrates Raman spectra 400 of amorphous film and non-crystalline graphene on $SiO_2$. Raman spectroscopy of the isolated film showed no 2D peak (2700 cm-1), but instead showed broad G (at ~1600 cm-1) and D peaks (at ~1350 cm-1). The broadening of D and G peaks usually indicates a transition from nanocrystalline graphene to amorphous film as was previously reported.[1] From the intensity ratio of the D and G peaks, the domain size is estimated to be in the order of 1-5 nm.[1] Raman spectroscopy serves as a characterization tool to represent the TEM image in FIG. 2 in large area.

Figure 5:
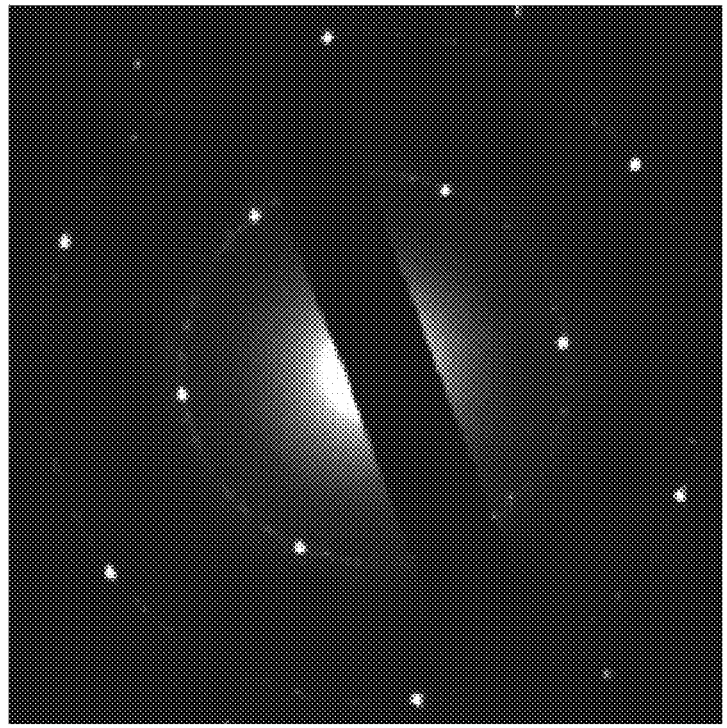
FIG. 5 illustrates TEM diffraction of atomically thin amorphous carbon (left) and graphene (right), according to one embodiment of the present disclosure.
Figure 5:
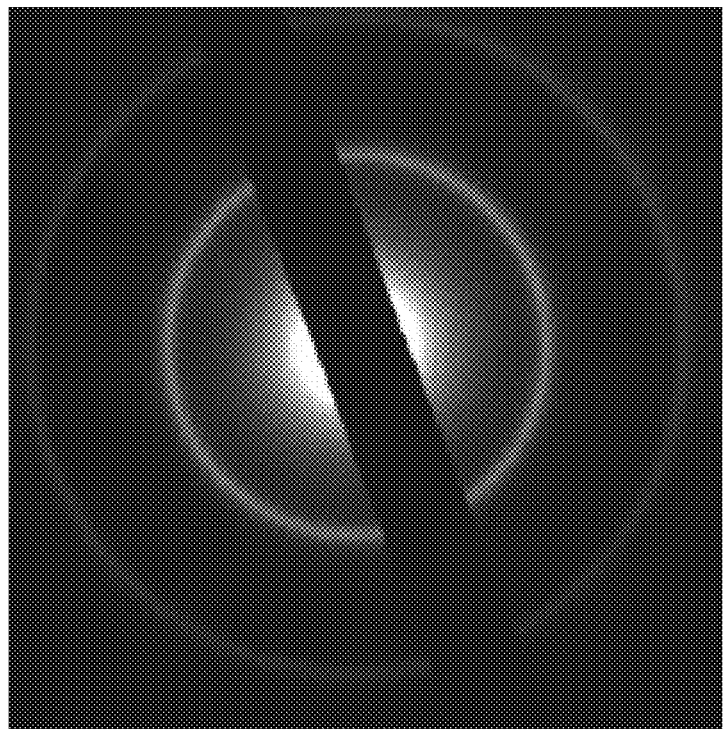

FIG. 5 provides a comparison 500 of TEM diffraction of atomically thin amorphous carbon (left) and graphene (right), according to one embodiment of the present disclosure. Further evidence on the amorphous nature of the disclosed isolated film is corroborated by the TEM diffraction, where no clear diffraction spots are detected which is in contrast to graphene wherein diffraction spots are clearly seen indicating crystallinity. The diffraction rings in FIG. 7 (top) indicates a domain size of <5 nm. The diffraction data of the amorphous film is consistent with the FFT image in FIG. 2. In this case, the 2DAC film is free-standing.

Figure 6:
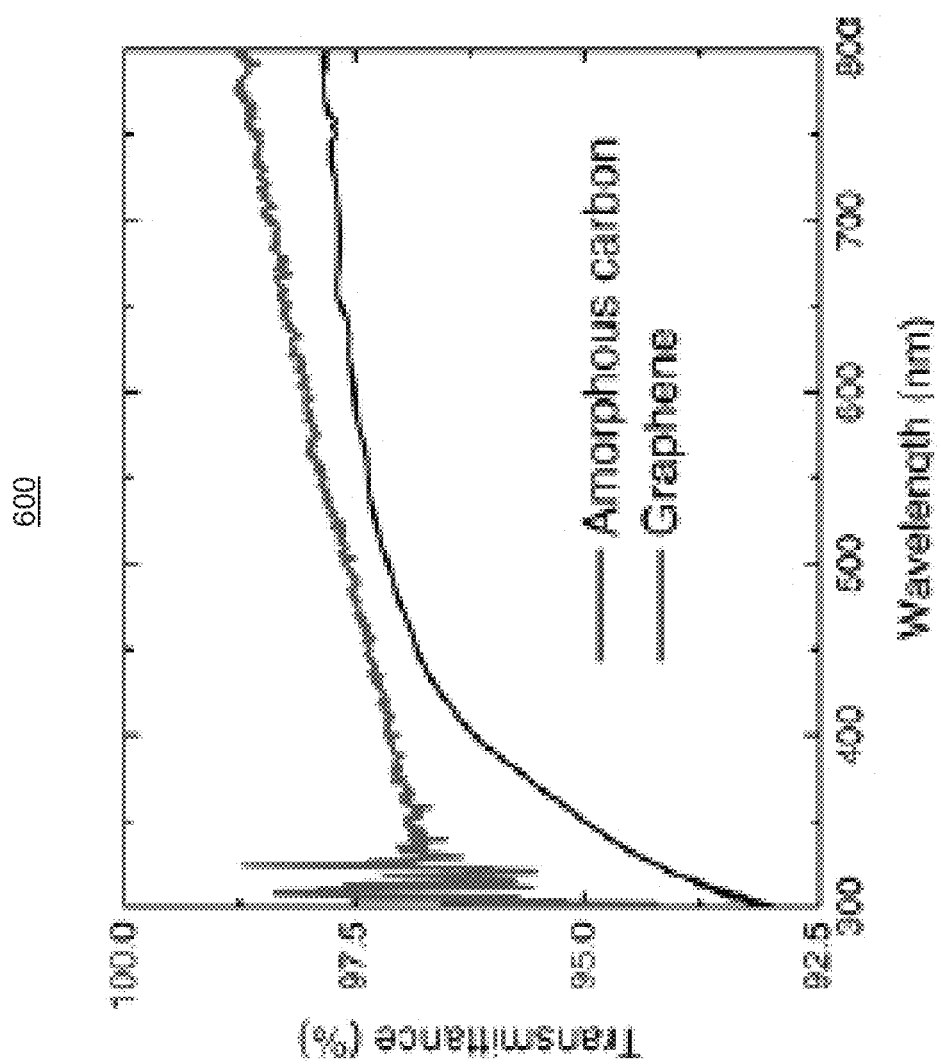
FIG. 6 illustrates the transmittance of the disclosed carbon film, according to one embodiment of the present disclosure.

Turning to FIG. 6, a graph 600 illustrates the transparency of the disclosed carbon film, according to one embodiment of the present disclosure. The optical transparency is at 98% at 550 nm light wavelength, increasing in transparency with increasing wavelength. Thus, select embodiments provide an optical transparency equal to or greater than 98% at a wavelength of 550 nm or higher. Again, the disclosed carbon film differs from graphene as the transparency of graphene at a single layer is at a maximum of 97.7% throughout the visible wavelength (400 nm-700 nm, inclusive), and decreases as the number of layer increases. Notably the transparency of the 2DAC film does not decrease rapidly at short wavelengths (<400 nm) as seen in graphene.

Figure 7:
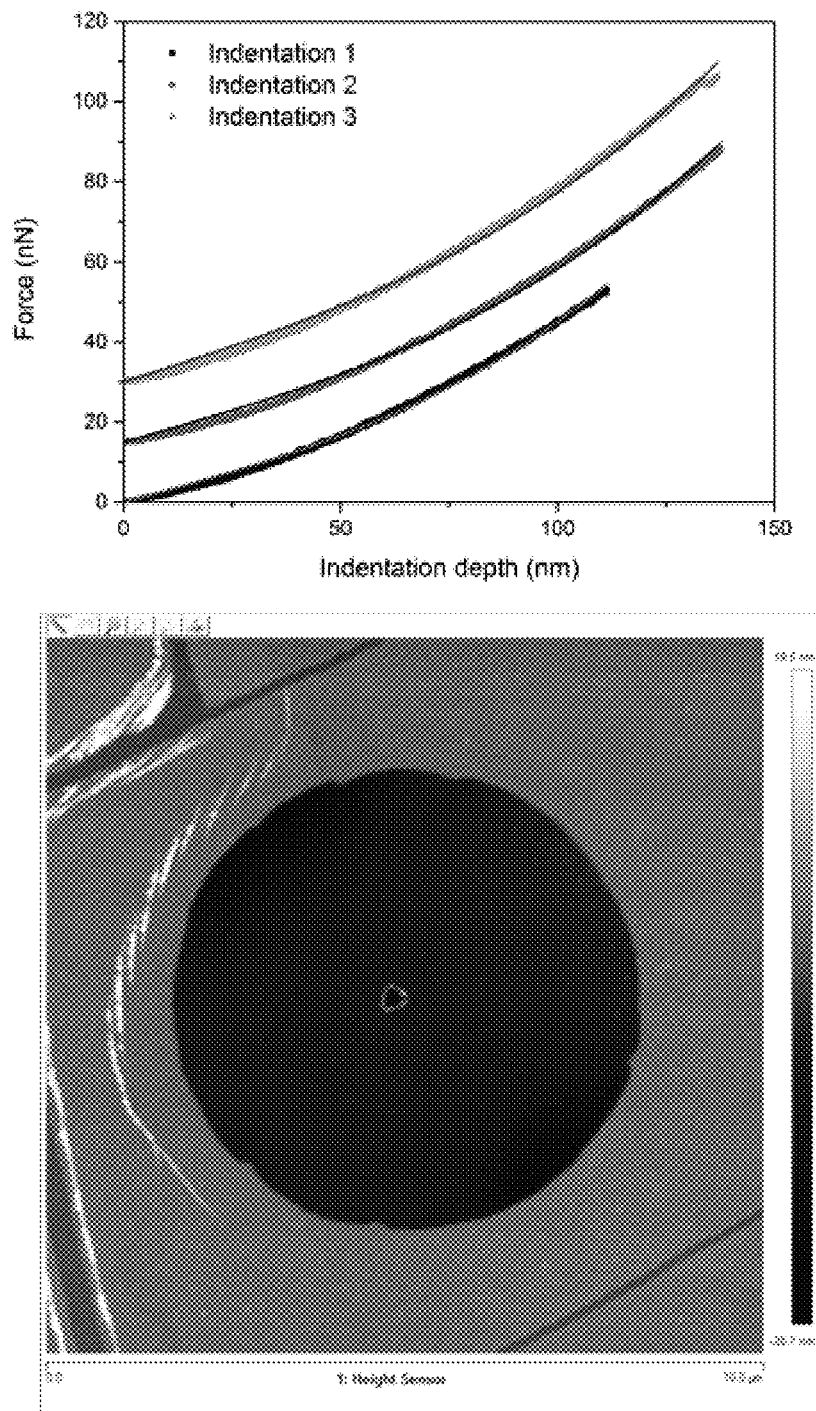
FIG. 7 illustrates a mechanical property of a 2D amorphous film and a demonstration of suspended carbon film, according to one embodiment of the present disclosure.

The elastic modulus, E, of the suspended film is above 200 GPa, higher than bulk glassy carbon (E=60 GPa).[2] The ultimate strain before mechanical failure is 10%, much higher than that of other amorphous carbon reported. FIG. 7 illustrates non-indentation on suspended carbon film and suspended carbon film after exertion of ultimate stress by an Atomic Force Microscope (AFM) (e.g., Bruker model no: MPP-11120) tip. The amorphous property of the disclosed 2DAC film prevents collapse of the suspended film in FIG. 7 (bottom). Instead, the film displays a ductile response to ultimate stress levels.

Figure 8:
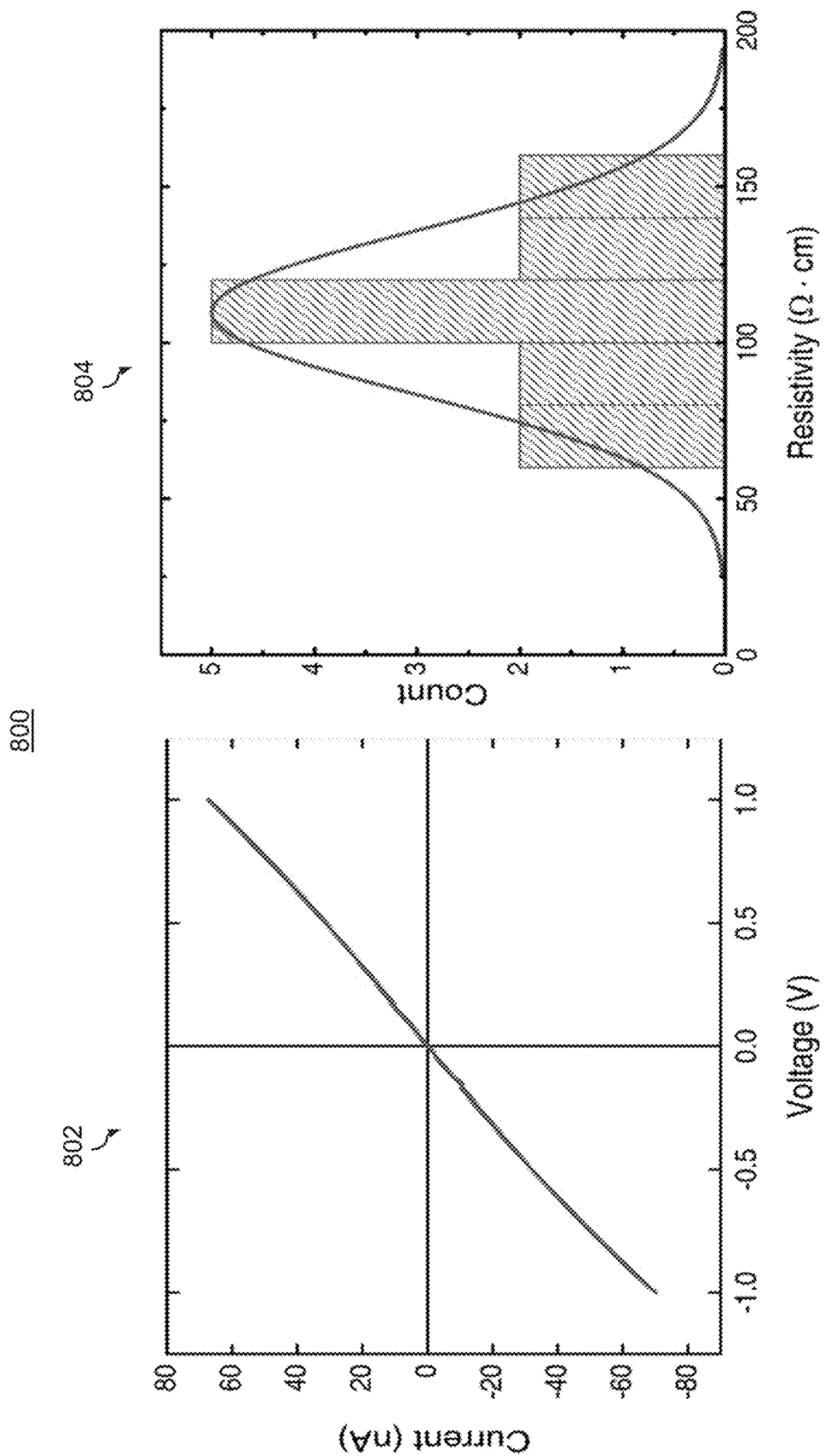
FIG. 8 illustrates electrical properties of a 2D amorphous carbon, according to one embodiment of the present disclosure.

The 2DAC thin film of the disclosed invention is highly resistive with electrical resistivity ranging from 0.01 to 1000 Ω-cm, depending on the value of C, which is tuned by the growth conditions. FIG. 8 is a schematic illustration 800 of electrical properties of a 2D amorphous carbon, showing an I-V curve 802 of the 2D amorphous film and a histogram 804 of the measured resistivity values for a particular C value. A measurement technique/method is used towards generating a resistivity value. A ratio is used within the calculation from the data of I-V curve 802 to obtain each resistivity data point in histogram 804. Accordingly, length:width ratio for the 2D amorphous carbon in FIG. 8, left is 1:100. In comparison, graphene has resistivity value of $~10^{-6}$ Ω-cm while bulk glassy carbon (also 100% C-C $sp^2$) has values ranging from 0.01 to 0.001 Ω-cm.

The monolayer film, containing n-membered rings >6, is naturally a membrane that can selectively pass gases, ions, liquids or other species whose sizes are small enough to pass through the 7-,8-,9-membered rings. In particular, the disclosed 2DAC film can pass through proton 10× more efficient than crystalline monolayer boron nitride at room temperature.[3] For the disclosed 2DAC film, the resistivity to proton flow across the membrane is from 1-10 Ω-cm$^2$ at room temperature.

Figure 9:
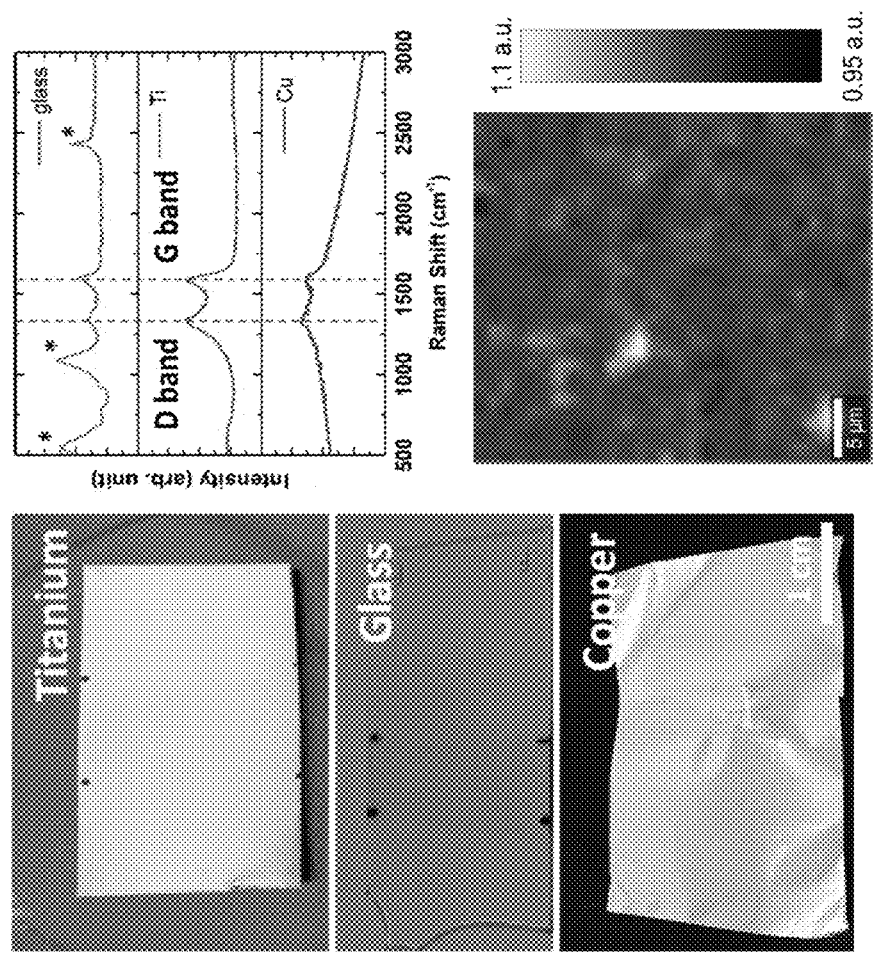
FIG. 9 illustrates composite material grown on different substrates, according to one embodiment of the present disclosure.

FIG. 9 illustrates composite material grown on different substrates, according to one embodiment of the present disclosure. Pictures of titanium, glass and copper coated with atomically thin amorphous carbon are illustrated on the left. In the upper right, shown is the Raman spectra from the coated regions showing similar response irrespectively of the substrate. Finally, in the lower right, shown is the Raman map of G/D peak ratio of the 2DAC film on top of the titanium shown its full coverage. The disclosed composite material (i.e., the disclosed 2DAC and the substrate) can be created from any metal (catalytic or non-catalytic) or on glass or oxides. Thus, disclosed embodiments provide that the 2DAC may be grown directly on any of the disclosed desired substrate materials. This is different from graphene, which can only be grown on a catalytic substrate, e.g., copper, and requires transfer to all other substrates. Accordingly, compared to deposition methods of amorphous or diamond-like carbon, whose thickness cannot exist lower than 1 nm to still be considered continuous, the disclosed composite material comprises an atomically thin (<1 nm) and continuous layer of two dimensional amorphous carbon that is strongly bonded to a host substrate.

In general, when a film on a substrate has poor adhesion, areas of the film may become detached from the substrate and, therefore, will provide poor or little protection of the substrate. Accordingly, embodiments of the present disclosure provide an improved film which provides uniformity and strong adhesion over the entire applied surface of a substrate. Accordingly, the disclosed 2DAC film is formed as a continuous film over, preferably, substantially the entire substrate surface or at least the applied surface. Unlike conventional designs, such as graphene, for example, in Cu, which can be detached easily (e.g., the adhesion force is from 10-100 J/m2), the disclosed atomically thin 2DAC film disposed, for example, on Cu adheres very well to the substrate with an adhesion energy >200 J/m2.[4] This example provides further evidence to differentiate the disclosed 2DAC film from graphene. (While an exemplary embodiment of a Cu substrate is described, embodiments of applying the disclosed 2DAC to any substrate may be applied in accordance with disclosed embodiments of the invention.) Furthermore, the adhesion energy is evident in all substrate materials onto which the disclosed 2DAC film is grown including, for examples, stainless steel, titanium, glass, nickel, and aluminum substrates. It should be appreciated that the above substrates are exemplary and the teachings of this disclosure may be applied to any substrate desired.

In general, any attempts for transferring any 2D material to a material by convention materials and processes have previously led to defects and cracks, for example, in the transferred material(s) and also a reduction of coverage on the substrate. This is, at least in part, due to the fact that the transfer process generally employs many mechanical steps and may use chemicals that induce cracks and defects in conventional film applications. The disclosed 2DAC film, however, does not need to be transferred, for example, from a growth substrate to a target substrate. In addition to the improved adhesion properties of the disclosed 2DAC film, enhanced characteristics of the disclosed 2DAC film provide and ensure consistent and full coverage directly across/over the substrate. Consistent and full coverage is thereby obtained, at least, because, there is no need to transfer the disclosed 2DAC film, since it is fully capable of consistently and successfully being grown directly on its host substrate.

Designed to provide such dependable coverage, together, along with its superior mechanical properties for adhesion to substrates (such as carbon), the disclosed 2DAC film is very suitable and dependable for applications that require additional physical characteristics/requirements of the 2DAC film and composite. Such physical characteristics may include the ability of the disclosed 2DAC film and/or composite to bend and/or stretch. The adhesion properties and ability of the disclosed 2DAC to the substrate ensures this is the case. If there is non-uniform adhesion to the substrate, like for transferred films, cracks in the film will form at regions of poor adhesion and are causes prone to failure.

Accordingly, embodiments of the disclosed invention provide the top amorphous carbon film 102 covering the whole substrate 104 upon which it is grown (Raman map of FIG. 9) making it very useful for applications that require, for example, carbon coating. The top amorphous carbon film 102 also serves as a diffusion barrier without defects thereby preventing the underlying substrate from oxidation and corrosion. Due to electrically insulating properties, the disclosed amorphous carbon film 102 prevents any galvanic corrosion of substrate 104. The low electrical conductivity of the disclosed 2DAC is beneficial to cell attachment and proliferation as observed in recent reports.[17] Cells on conductive substrates adhere to the surface through electrostatic interactions without creating focal adhesions. Focal adhesions are crucial to cell proliferation and growth and a low electrical conductivity is preferred for focal adhesion development and cell proliferation. The low electrical conductivity is a consequence of the amorphous nature of the disclosed 2DAC as observed through the Raman spectroscopy D/G peak intensity and the sp$^3$/sp$^2$ ratio.

In contrast, graphene is known to worsen long term corrosion.[5] The transfer of graphene makes it nearly impossible to create a flat continuous film without creating cracks and defects along the surface. The disclosed amorphous carbon film 102 material is a composite with substrate 104, hereby eliminating the need for transfer as well as removing the risk of cracks in the film 102.

Figure 10:
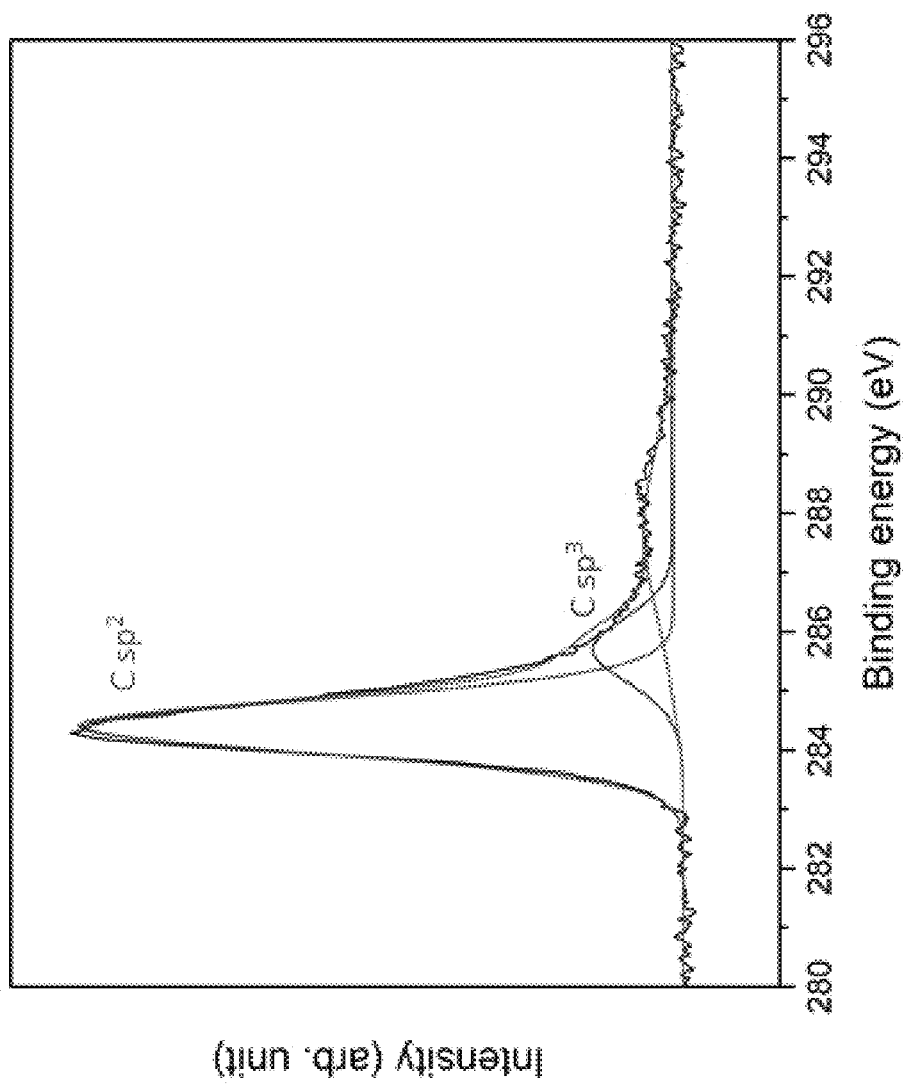
FIG. 10 illustrates X-ray photoelectron spectroscopy (XPS) of a 2D amorphous carbon on Cu, according to one embodiment of the present disclosure.

The disclosed 2DAC film consists of sp$^2$-bonded carbon similar to glassy carbon; however the thickness is only approximately one atomic layer thick (6 Å), thinner than any conventional reported amorphous carbon structure. FIG. 10 illustrates the X-ray photoelectron spectroscopy (XPS) measurement of 2D amorphous carbon on Cu, where the peak position indicates the sp$^2$ or sp$^3$ bonding type while the peak intensity indicates the fraction of each type of bonds. A mix concentration of C-C sp$^2$ and sp$^3$ bonding is also possible without sacrificing the thickness, though the maximum C-C sp$^3$ content is set to 20%. The thin structure and strong adhesion of the disclosed 2DAC intrinsically protects the underlying substrate all the time, unlike in thicker films where the possibility of flaking off is evident.[6]

According to disclosed embodiments, a laser-based growth process, using hydrocarbons as precursors (such as $CH_4$, $C_2H_2$, etc.) produces the disclosed composite film. Hydrogen gas ($H_2$) and Argon gas (Ar) may also be mixed with the precursor. In this process, the laser has two roles: (1) an energy source to breakdown the precursor gas in a process called photolytic decomposition; and (2) as a local heat source. Assuming that one or both aforementioned roles produces the disclosed 2DAC film: in the first case, the substrate 104 is said to be at room temperature throughout the growth; in the second case, the laser can heat up the substrate 104 up to 500° C. Typically, a pulsed excimer UV laser (e.g., 193, 248 or 308 nm) can be directed onto or parallel to the substrate at a fluence from about 50-1000 mJ/cm$^2$ at different growth times, depending on the employed substrate. Other possible combinations to produce the disclosed composite may include utilizing any combination of a laser, plasma, and/or a substrate heater. A heater may be employed to heat the substrate 104 up to 500° C. Plasma power may be used in the range of and including 1-100 W. A typical combination using hydrocarbon as precursor will be as follows: (i) Laser only; (ii) Laser+low power plasma (5 W); (iii) Laser+low power plasma (5 W)+heater (300° C.-500° C.); (iv) Low power plasma (5 W)+500° C. heater; (v) High power plasma (100 W) only.

Accordingly to disclosed embodiments, the entire growth/deposition of the disclosed 2DAC and 2DAC composite may be performed within a chamber. Modules for heating, plasma, gas flow and pressure control may all be set and established within the chamber for the controlled growth environment. According to one embodiment, the process pressure of the chamber may be established in a range of, and including, 10 to 1E-4 mbar.

EXAMPLES

Example 1

Example Subject Matter

The process parameters for the disclosed 2DAC may include the following: (i) process gas: CH4 (ii) chamber pressure: 2.0 E-2 mbar; (iii) laser fluence: 70 mJ/cm$^2$; (iv) growth time: 1 min; (v) plasma power: 5 W; (vi) substrate: Cu foil.

A process for producing the disclosed 2DAC film of Example 1 employs the use of methane (CH4) within the growth chamber for the growth process. The gas pressure within the chamber during the growth is controlled at 2 E-2 mbar throughout. This gas is in the presence of a plasma generator operating at 5 W power. The growth starts when the 248 nm excimer laser is exposed on the surface of the copper foil substrate with a fluence of 70 mJ/cm$^2$ with a pulse frequency of 50 Hz. The laser exposure time (i.e., growth duration) is set at 1 min to obtain a continuous 2DAC coating on the substrate. In this growth, the stage heater is not used. Multiple parameters disclosed herein may be adjusted, for controlling and/or changing the properties of the disclosed 2DAC including, but not limited to, hydrocarbons as precursors, precursor mixes, adjustments to the photolytic decomposition process and equipment, temperature regulations, substrate temperature adjustment, the change in C value, change in number of atomic layers, change in sp$^2$ to sp$^3$ ratio, and change in adhesion to substrate.

Advantages of the disclosed embodiments may be implemented in a wide variety of applications. In one application, biological implants are used to treat several diseases including, for example, coronary heart disease, physical trauma and dental decay. A key part of a functioning biological implant is compatibility with the surrounding tissue. Common issues with implants may include rejection by a host tissue, inflammation and blood thrombosis. Coating a metal implant with a carbon coating has been shown to render such devices biocompatible thereby reducing the effects of the aforementioned complications. Attempts to provide prior-art coatings have suffered from long-term degradation for various reasons including detachment of the coating and/or mechanical breakage of the coating itself. This may lead to several medical issues such as thrombogenisis of cardiac stents[7] as well as corrosion and mechanical failure of stents and bone implants.[8] The composite described by the present disclosure may be constructed of metal, glass, ceramics, and/or plastic 104 and atomically thin carbon film 102 thereby making the substrate material biocompatible and ready for several biomedical applications. These biomedical applications may include applications as in stents, screws, heart valves, dental implants, etc. The thickness of prior art coatings causes stress-mismatch in specific biomedical applications such as during bending of stents. The aforementioned stress-mismatch may cause cracks in the coating, for example, of biomedical devices and produce incomplete coverage to the surface of the same.

The disclosed carbon film may be constructed with minimal thickness thereby ensuring that the disclosed metal surface of the substrate is consistently and completely covered during the lifetime of applied usage. In one exemplary embodiment, the disclosed 2DAC thickness may be designed at approximately one atomic layer thick. The disclosed carbon film 102 may be grown directly on several substrates 104, for example, such as those already employed in biomedical applications such as stainless steel and titanium materials. Since the growth is done at much lower temperature than, for example, graphene synthesis, the disclosed 2DAC may be grown directly to other substrates 104 that cannot withstand high temperature like glasses and hard discs.[9] The disclosed 2DAC film 102 is ultra-strong and is strongly bounded to the substrate 104 making it suitable for applications that may require deformation such as bending and stretching. The strong mechanical properties of the disclosed 2DAC film is due to its lack of grain boundaries. The insulating property of the disclosed carbon film 102 prevents galvanic corrosion of the substrate 104 unlike graphene which enhances the corrosion. The 7-,8-, and 9-membered rings of the carbon film, as seen in the TEM image, is useful as an efficient membrane for gases or for proton transport.[3]

Disclosed embodiments of the carbon film 102 and substrate 104 may be employed in other applications including, but not limited to: biomedical technologies, for example, exercising the use of metals requiring carbon coating for biocompatibility. Exemplary embodiments may include being utilized as stents, dental implants (e.g., teeth), orthopedic implants etc. Aside from implants, disclosed embodiments may be used as a culture substrate for stem cells and muscle growth. In yet another embodiment, the disclosed carbon film and substrate material may be useful as an ultra-thin anti-corrosion coating for high density hard discs. In another application, the disclosed carbon film and substrate material may be utilized as an efficient gas membrane or for proton transport. Any limitation of the disclosed coating is the discrete nature of the application itself, i.e., the metal is either carbon coated or not.

According to select embodiments of the disclosed invention, the disclosed 2DAC may be generated as a free-standing case, for example, when a substrate is not suitable to be grown on, and hence the disclosed 2DAC needs to be transferred. However, advantages of the present disclosure provide that the disclosed 2DAC is directly grown on a substrate. Such benefits of the disclosed 2DAC film compared, for example, to graphene for the transfer process is that the disclosed 2DAC film does not require a sacrificial support layer for transfer (unlike graphene). With graphene, the film layer is required to prevent cracks and defects during the transfer, and the film layer needs to be removed after. Even with removal, there residues remain from the sacrificial layer that cannot be completely removed. With the disclosed 2DAC, the transfer can be done without the sacrificial layer, without inducing defects and without dealing with residues or compromising the structure.

Competing methods include drug eluting polymer coatings, which can increase biocompatibility and help medicate the local region. Increased coating of these polymers, for example, by the disclosed 2DAC, may carry increased amount of drugs and therefore have an advantage over the carbon coating.

As mentioned earlier, an important application of the disclosed carbon film and substrate material in a biomedical application includes an application in stem cell and muscle growth. The use of stem cells in tissue engineering has in recent years received enormous interest due to the therapeutic and regenerative potential of these cells. This potential arises from a combination of prolonged self-renewal in an undifferentiated state and the pluripotency of the cells, namely the ability to differentiate into several different lineages. The stem cells can differentiate into all somatic cells in the body. A cell harvested from the bone marrow of a patient could thus be used to treat and regenerate damaged tissue and organs.

Growing and maintaining stem cells in an undifferentiated state is a difficult and slow procedure by current state of the art methods. Furthermore, the current techniques utilize mouse embryonic fibroblast layers or gelatinous protein mixture secreted by mouse tumor cells (Matrigel), thereby introducing xenogeneic proteins. The techniques are thus not suitable for therapeutic efforts due to the risk of xenogeneic contamination.

The growth of stem cells on feeder cells is both a complicated procedure and unsuited for clinical use. The complications arise from the laborious preparation procedure, high cost and batch-to-batch variability in the outcome. The stem cells are not suitable for clinical use due to possible xenogeneic or viral contamination from the feeder layer.

Commitment to specific lineage depends on several factors arising from the local environment such as mechanical rigidity of the extracellular matrix (ECM), chemical growth factors and neighboring cells.[10, 11] Controlling the fate of the stem cells is a critical goal to reach for the use of stem cells in a clinical setting. While biochemical inducers have shown to be able to activate pathways directing the lineage of the cells[12], recent research has shown promise by simply modifying the mechanical environment of the cells, hereby activating cues for the cell to commit to specific lineages.[13, 14, 15]

Further, the differentiation and growth of stem cells is often inhibited due to a lack of bioactive substrates.

Lastly, chemical factors such as BMP-2 are a labor intensive because they are required to be administered every 3 days during cell culture, thereby increasing the material costs, interaction with the cells, and labor costs.

Example embodiments of the disclosed invention provide a two-dimensional amorphous carbon (2DAC) bioactive substrate coating and methods of growing and differentiating stem cells.

Example embodiments of the disclosed invention provide a 2DAC coating having an atomic structure consisting of non-hexagonal carbon rings and hexagonal carbon rings, wherein a ratio of the hexagonal rings to the non-hexagonal rings is equal to or less than 0.8.

According to example embodiments of the disclosed invention, the coating of implants with 2DAC can enhance the biocompatibility and reduce inflammation of the host tissue.

According to example embodiments of the disclosed invention, the coating of substrates with 2DAC can prevent bacterial growth and can reduce bacterial infections at the site of an implant.

Example embodiments of the disclosed invention provide a method of growing stem cells, including coating a surface of a substrate with 2DAC, seeding an initial concentration of stem cells on the surface of the substrate coated with 2DAC, and growing additional stem cells from the seeded stem cells until a desired concentration of the stem cells is reached.

In one example the stem cells are seeded onto the disclosed 2DAC coated surface at a density of 10,000 cells/cm$^2$ in low-glucose Dulbecco's modified eagle medium with 10% FBS, 1% penicillin, 1% non-essential amino acids and 1% sodium pyruvate. The cells are cultured at 37° C. and 5% CO2. The coating may be referred to as directly growing on the 2DAC. Thus, an implant coating is established on the disclosed 2DAC coated surface. The medium is replaced every 3 days until desired concentration is reached. In some disclosed embodiments, the implant can be a coronary stent, dental implant, orthopedic implants, etc.

The seeded cells have a better recovery rate on the disclosed 2DAC surfaces compared to other cell culture surfaces. The cells display a faster rate of attachment to the disclosed 2DAC compared to other substrates or standard tissue culture substrates, thereby reducing the cell death occurring from a lack of anchorage. The implant coating may form a contact angle with the surface of the implant. In some disclosed embodiments, the contact angle of the 2DAC surface is between approximately 30-65 degrees and is optimal for cell growth.

Example embodiments of the disclosed invention provide a method of differentiating stem cells into specialized cells, including coating a surface of a substrate with 2DAC, seeding an initial concentration of stem cells on the surface of the substrate coated with 2DAC, and adsorbing growth factors in a stem cell medium onto the surface of the substrate coated with the disclosed 2DAC. Accordingly, growth factors are automatically adsorbed onto the surface of the disclosed 2DAC during culturing cells. Disclosed embodiments provide that growth factors are automatically adsorbed onto the disclosed 2DAC surface at a higher rate as compared to a non-coated surface.

In one example the stem cells are differentiated towards osteogenic lineage by adding dexamethasone, L glutamine, ascorbic acid and β-glycerophosphate to the medium. The cells are cultured at 37° C. and 5% CO2. The medium is replaced every 3 days.

The growth factors are adsorbed onto the disclosed 2DAC surface at a higher rate compared to a non-coated surface. The free pi-orbitals of the sp$^2$ bonded carbon atoms in the disclosed 2DAC create bonds with the osteogenic factors dexamethasone and β-glycerophosphate. This adsorption increases the availability of the factors driving the osteogenic differentiation to the stem cells, leading to increased uptake and differentiation in the cells.

According to example embodiments of the disclosed invention, the substrate can be materials for in vitro or in vivo stem cell growth and differentiation.

According to example embodiments of the disclosed invention, the disclosed 2DAC enhances the bioactivity of the substrate and accelerates the differentiation of the stem cell.

Example embodiments of the disclosed invention provide a 2DAC bioactive substrate coating that enhances biocompatibility between host tissue and an implant, and/or reduces inflammation of the host tissue.

Example embodiments of the disclosed invention provide a 2DAC antibacterial coating that reduces bacteria attachment and proliferation.

Example embodiments of the disclosed invention provide a method of growing stem cells that sustains xenogeneic-free growth and proliferation of stem cells, and accelerates the differentiation into specific lineage.

Example embodiments of the disclosed invention relate to an article and method of sustaining stem cells in an undifferentiated state, an article and method of inducing differentiation of stem cells toward a specific lineage and a coating for biomedical implants.

The article consists of a coating of the disclosed 2DAC on an arbitrary substrate (metal, glass, plastic) as described in the patent document by Orofeo et al. entitled "Layered composite material consisting atomically thin amorphous carbon on top of the substrate" (the entire contents and disclosures of this patent document is incorporated herein by reference in its entirety) and coats the entirety of the surface. The disclosed 2DAC is a single layer of carbon atoms in a non-crystalline structure, having a C-value below or equal to 0.8. The C-value is a ratio of the hexagonal rings to the non-hexagonal rings.

Figure 11:
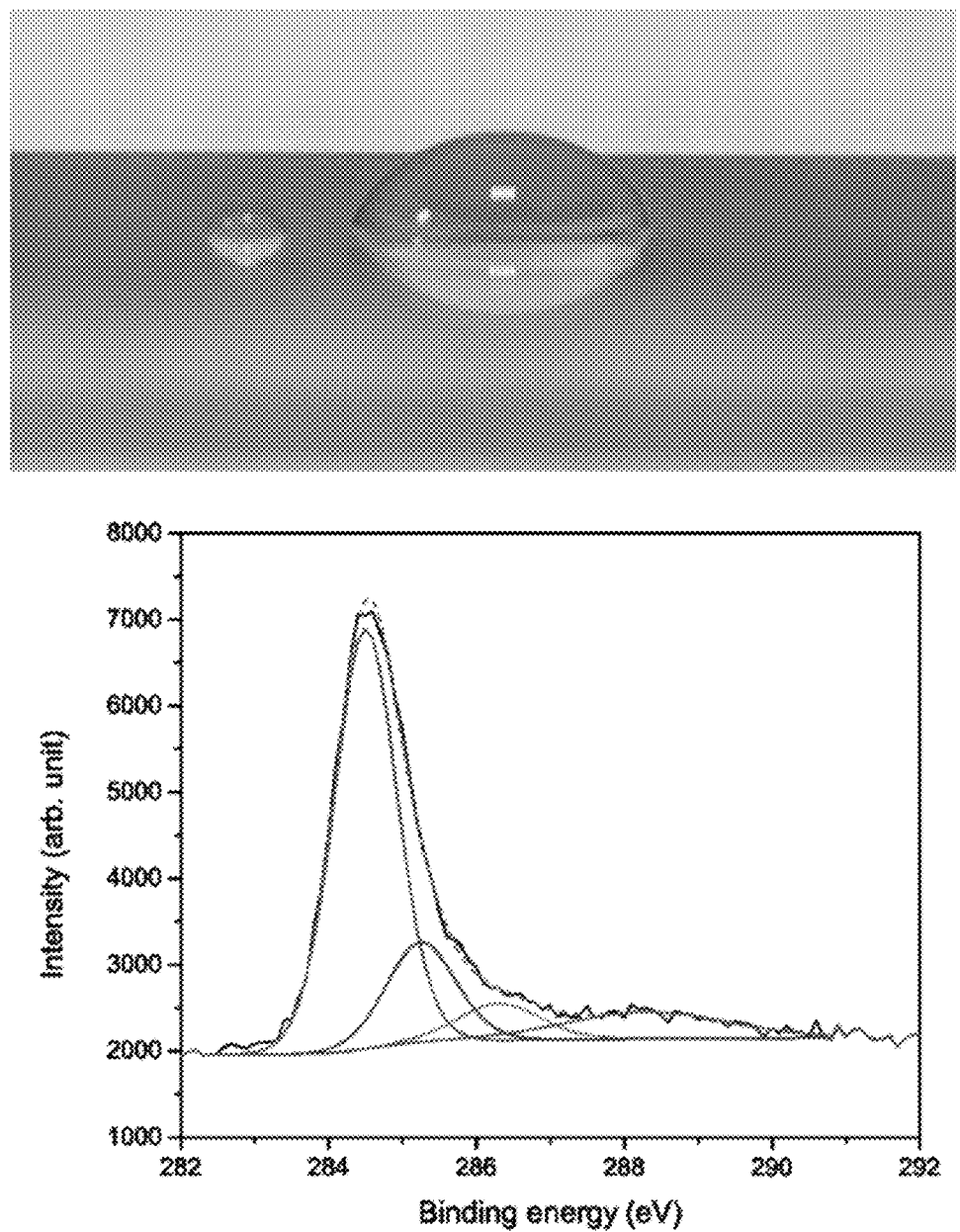
FIG. 11 shows a water droplet contact angle and XPS for 2DAC, according to one embodiment of the present disclosure.

FIG. 11 shows a contact angle and XPS for 2DAC.

Referring to FIG. 11, a contact angle for 2DAC is about 60 degree, which is lower than the 90 degree contact angle reported for graphene.

The ratio of $sp^3/sp^2$ refers to the type of carbon bonds found in the disclosed 2DAC. The $sp^2$ bonds allow for higher growth factor bonding. The XPS for 2DAC in FIG. 11 confirms that the $sp^3/sp^2$ bond ratio is 0.2 or less.

Figure 12:
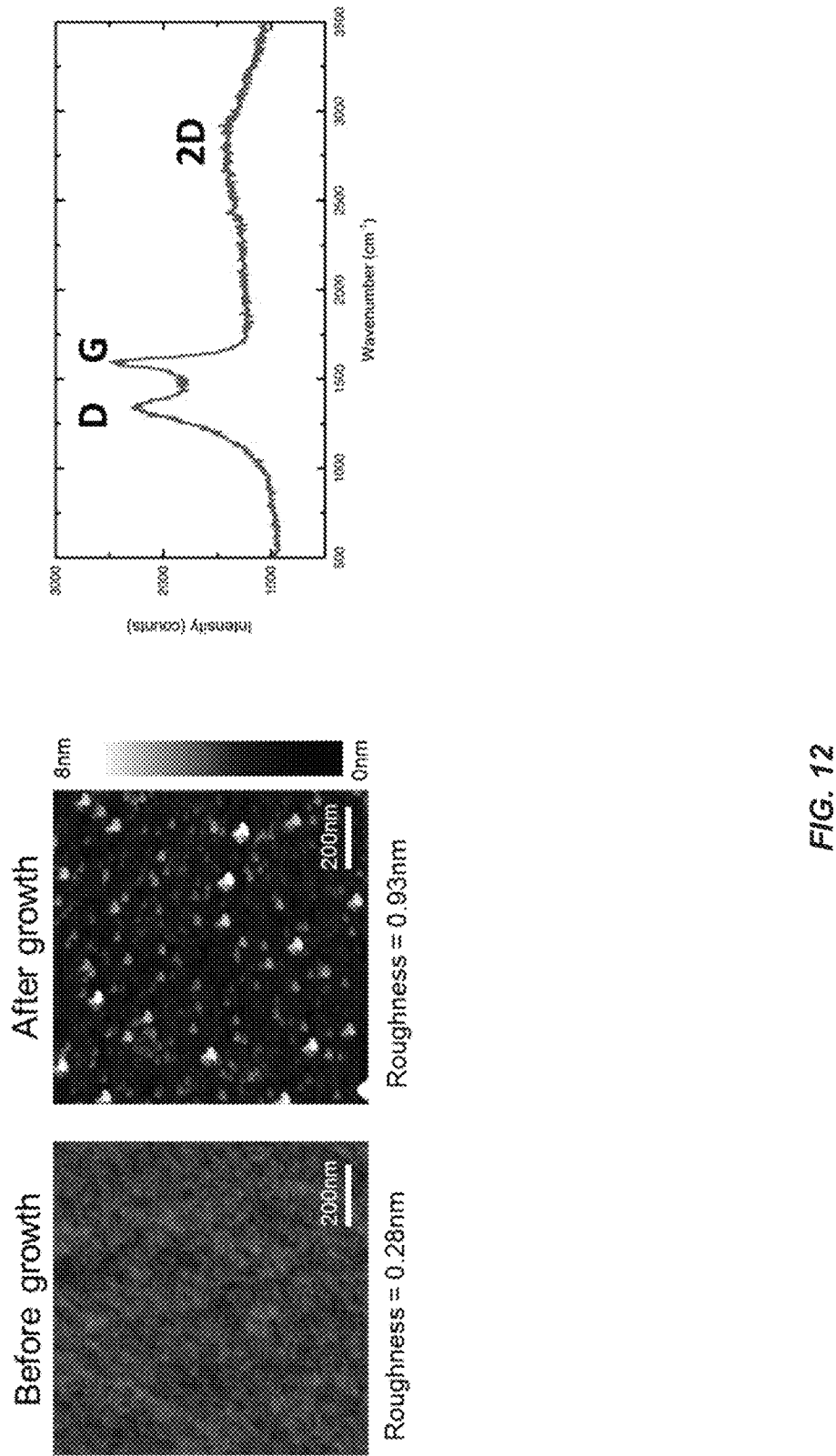
FIG. 12 shows the nano-topographical difference between uncoated glass and 2DAC coated glass, and a Raman spectra of the 2DAC coating, according to one embodiment of the present disclosure.

FIG. 12 shows the nano-topographical difference between uncoated glass and 2DAC coated glass. Referring to FIG. 12, the disclosed coating creates a roughness about 1 nm on the substrate, which enhances the cell-to-substrate interaction. The Raman spectrum in reveals a D/G-ratio of about 0.5-1 and displays the absence of 2D-peak. This ratio attributed to the disclosed coating combined with the absence of 2D-peak distinguishes the disclosed 2DAC differently from the structure of graphene and diamond coatings.

Example embodiments provide a method of growing and proliferating stem cells in a neutral state as follows.

Stem cells are seeded on the 2DAC coated surface and cultured in standard stem cell media until desired concentration is reached. The cells can be detached from the surface and diluted onto multiple surfaces for cell expansion. The rate of cell growth is equivalent or larger than that of fibroblast feeder layers or Matrigel.

The cells do not display any form of differentiation but remain in the neutral undifferentiated state. The nanoscale roughness and hydrophilicity of the 2DAC allows the cells to adhere and spread similar to what has been observed in nanocrystalline graphene.[16]

Example embodiments provide a method of controlling and accelerating the stem cell differentiation into desired lineage as follows.

Differentiation is induced by growth factors added to the stem cell medium. The growth factors determine the lineage. For example, for osteogenic differentiation, the growth factors would consist of dexamethasone and β-glycerolphosphate. The growth factors are readily adsorbed on the surface and delivered to the cells at an increased rate compared to standard tissue culture plates, glass or metal substrates. The mechanical properties of the amorphous carbon enhance the cell-to-substrate interaction which in turn enhances the differentiation.

Figure 13:
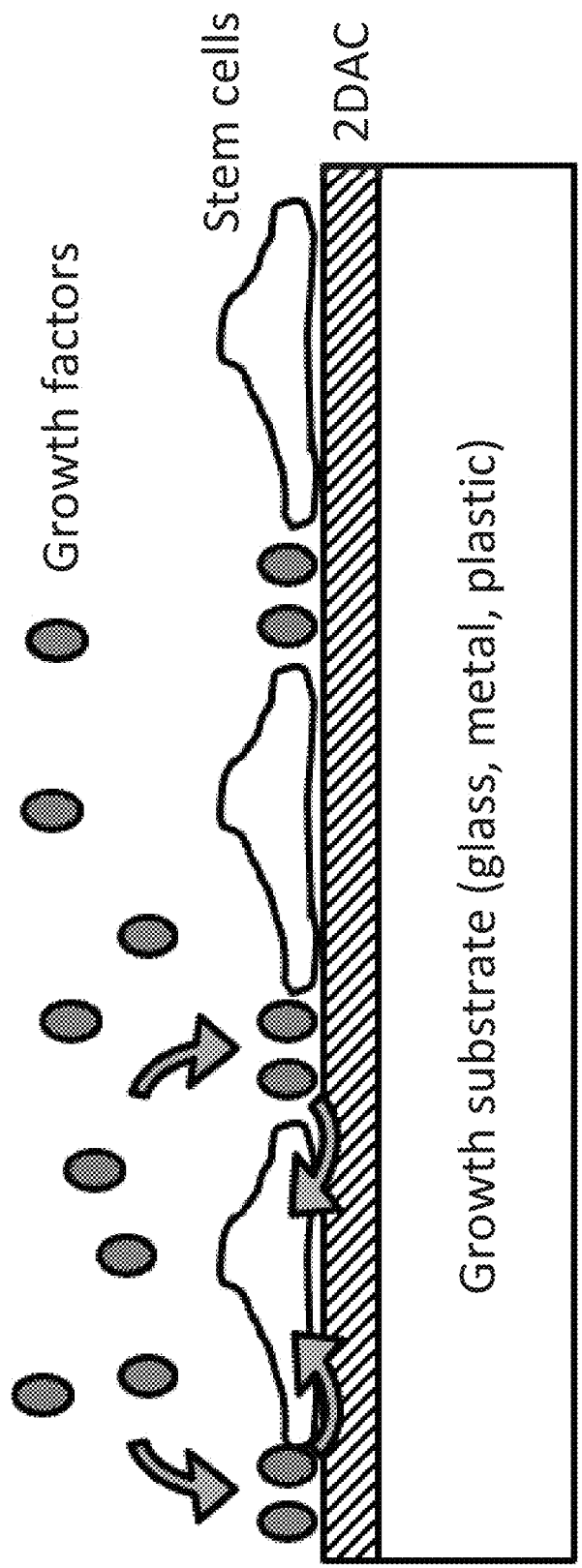
FIG. 13 shows a mechanism of increased uptake of growth factors in stem cells on a 2DAC coated substrate, according to one embodiment of the present disclosure.

As outlined above, growth factors are automatically adsorbed onto the surface of the disclosed 2DAC during culturing cells. Accordingly, disclosed embodiments provide that growth factors are automatically adsorbed onto the disclosed 2DAC surface at a higher rate as compared to a non-coated surface. FIG. 13 shows a mechanism of increased uptake of growth factors in stem cells on a 2DAC coated substrate.

Figure 14:
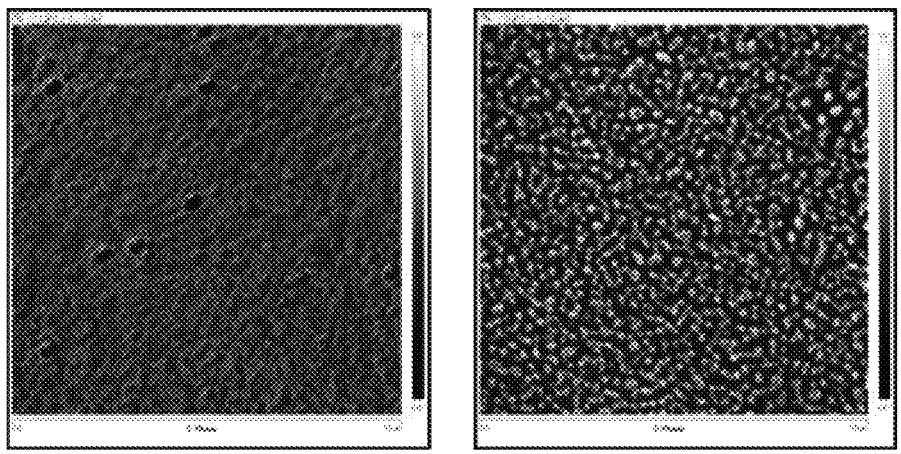
FIG. 14 shows a comparison of the protein uptake on a 2DAC coated substrate and a non-coated substrate, according to one embodiment of the present disclosure.
Figure 14:
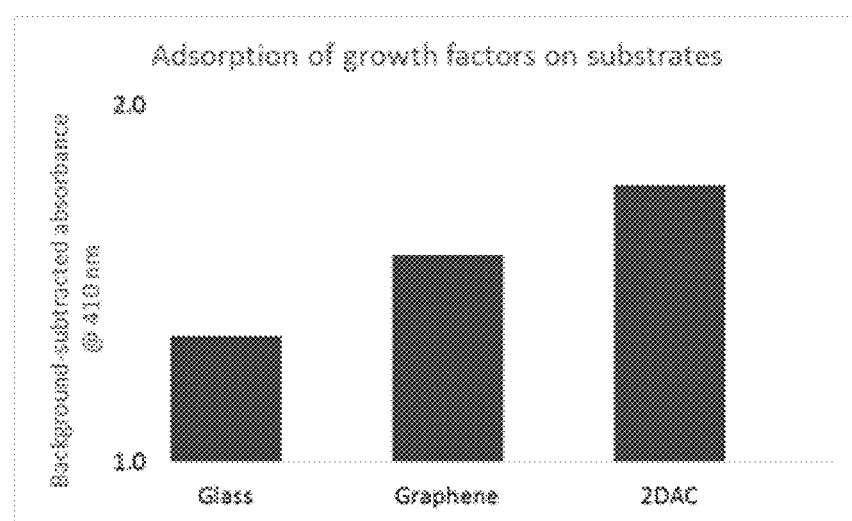

FIG. 14 shows a comparison of the protein uptake on a 2DAC coated substrate and a non-coated substrate. FIG. 14 illustrates an AFM phase scan of protein-functionalized non-coated titanium (upper left) and 2DAC-coated titanium (upper right). Adsorption of growth factors is enhanced on the disclosed 2DAC compared to other substrates (lower), i.e., the protein uptake on the disclosed 2DAC coated surface is significantly enhanced compared to non-coated substrates.

The AFM phase scan in FIG. 4 reveals a lack of protein on the uncoated titanium on the left, while the 2DAC-coated titanium on the right is readily adsorbing proteins. It should be appreciated that the while titanium is illustrated, other metals such as titanium alloys, stainless steel, gold, silver, cobalt-chromium alloys, niobium tantalum; ceramics such as aluminum oxide, titanium oxide, zirconium oxide, silicates, hydroxyapatites, calcium phosphates; and polymers such as polyethylene, polyamide, polymethylmethacrylate polytetrafluroethylene, among other materials, may be utilized without departing from the teachings of the invention.

Implants can be coated with 2DAC for increased biocompatibility and integration with local host tissue. This biocompatibility manifests itself in reduced inflammatory response from host tissue, reduced blood clotting and activation of platelets in exposed blood vessels, and/or enhanced growth of cells on the coated implant surface, thereby forming a stronger bond between tissue and implant.

Figure 15:
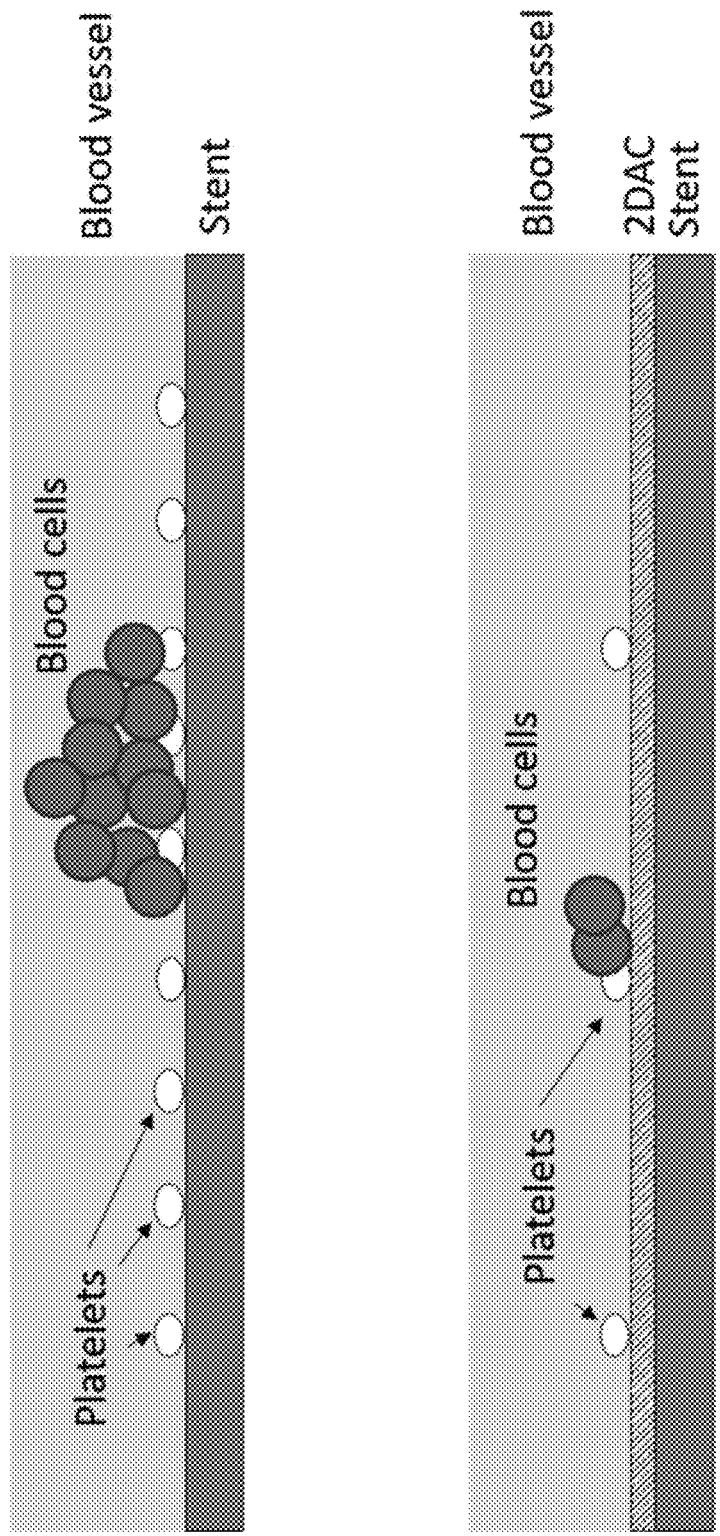
FIG. 15 shows a comparison of blood clotting prevention on a 2DAC coated stent and a non-coated stent substrate, according to one embodiment of the present disclosure.

FIG. 15 displays an uncoated and 2DAC coated surface of a cardiovascular stent implant. The uncoated cardiovascular implant can cause platelet attachment and activation. Activated platelets propagate coagulation factors causing a blood clot to form. The 2DAC coating reduces the attachment and activation of platelets and hereby, in turn, reduces the risk of thrombosis.

Figure 16:
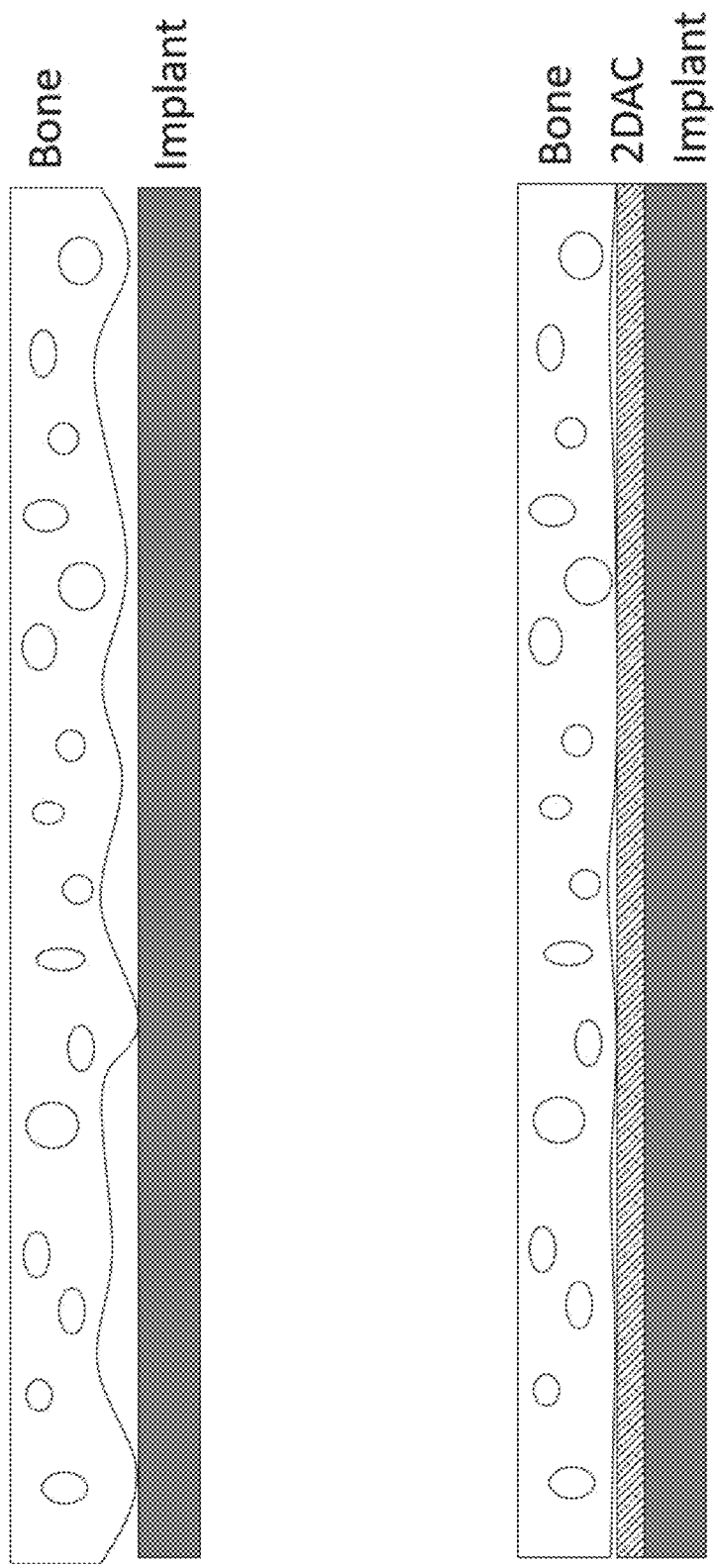
FIG. 16 shows a comparison bone tissue-to-implant integration, according to one embodiment of the present disclosure. The 2DAC coated implant provides better integration with the host tissue compared to a non-coated implant.

FIG. 16 displays how the 2DAC coating can improve the integration between implant and bone tissue. The 2DAC coating improves the cell attachment, reduces inflammation and enhances osteogenic differentiation of nearby cells. These factors leads to a stronger and continuous bond between implant and bone tissue.

Figure 17:
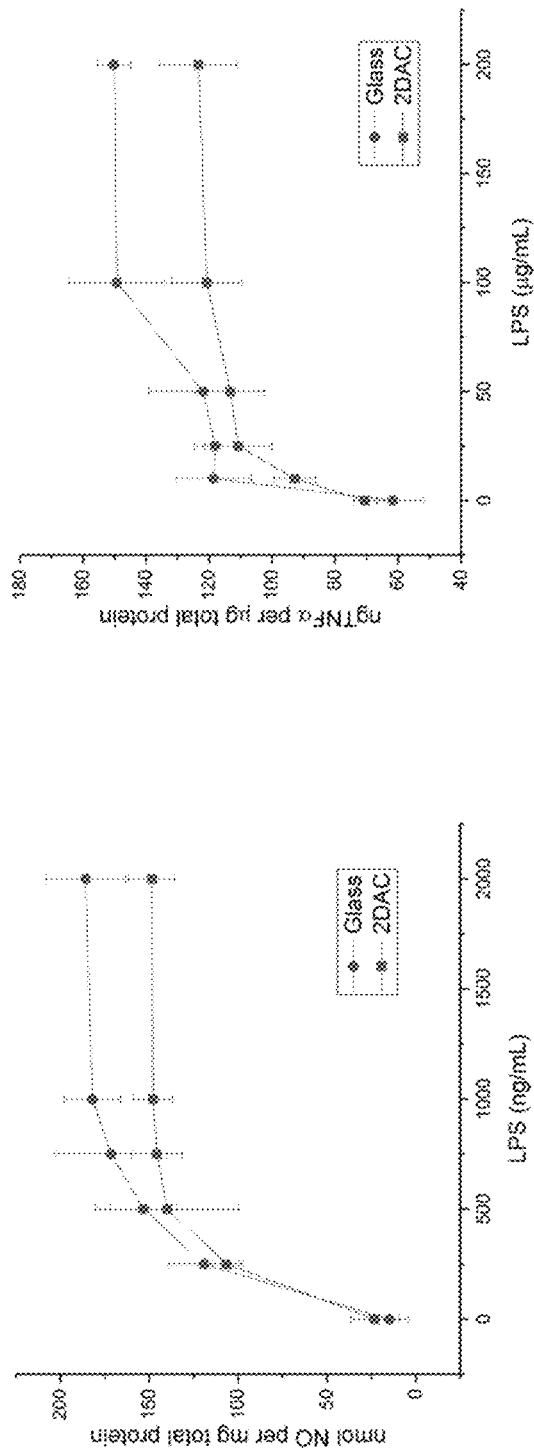
FIG. 17 shows comparisons for nitric oxide (NO) and TNFα production in cells stressed by LPS (Lipopolysaccharides) on a 2DAC coated glass compared to cells on bare glass, according to one embodiment of the present disclosure.

FIG. 17 shows comparisons for nitric oxide (NO) and TNF-α production in cells stressed by LPS (Lipopolysaccharides) on a 2DAC coated glass compared to cells on bare glass.

Both NO and TNF-α are indicators of systemic inflammation. The results shown in FIG. 5 indicate that the inflammation will be reduced.

By employing 2DAC as growth substrate, the practical difficulties and the labor time and costs are reduced, and the contamination concerns are eliminated.

The disclosed 2DAC can be directly grown on a substrate as outlined above. The direct growth of the amorphous carbon has the benefit of high adhesion strength to the substrate (with an adhesion energy of >200 J/m$^2$). On the contrary, chemical vapor deposition (CVD) graphene is required to be transferred to growth substrate and has a very poor adhesion of about 10 J/m$^2$.

The production of 2DAC may be scaled up to a large area directly on any substrate. The growth of the disclosed 2DAC may be carried out below 500° C. allowing it to be compatible with many biomedical implants and applications.

The disclosed amorphous carbon does not pose any toxicity issues for biological tissue and has already been approved for biomedical implants by the FDA. Furthermore, several carbon coated stents have been promoted for clinical use in Europe: BioDiamond® (Plasma Chem), Carbostent® (Sorin), Diamond Flex® (Phytis) and Dylyn® (Bekaert). Thus, 2DAC is suitable to be used in a clinical setting even though the 2DAC is different than a mere carbon coating, as discussed above.

Having described the many embodiments of the present disclosure in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

REFERENCES

The following references are referred to above and are incorporated herein by reference:

1. Ferrari, A. C. et al. "Interpretation of Raman spectra of disordered and amorphous carbon." *Physical Review B* 61, 14095-14107 (2000).
2. Robertson, J. "Ultrathin carbon coatings for magnetic storage technology." *Thin Solid Films* 383, 81-88 (2001).
3. Hu, S. et al. "Proton transport through one-atom-thick crystals." *Nature* 516, 227-230 (2014).
4. Das, S. et al. "Measurements of adhesion energy of graphene to metallic substrates." *Carbon* 59, 121-129 (2013).
5. Schriver, M. et al. "Graphene as a Long-Term Metal Oxidation Barrier: Worse Than Nothing" *ACS Nano* 7, 5763-5768 (2013).
6. Wang, J. S. et al. "The mechanical performance of DLC films on steel substrates." *Thin Solid Films* 325, 163-174 (1998).
7. Leng, Y. X. et al. "Mechanical properties and platelet adhesion behavior of diamond-like carbon films synthesized by pulsed vacuum arc plasma deposition." *Surface Science* 531, 177-184 (2003).
8. Maguire, P. D. et al. "Mechanical stability, corrosion performance of amorphous diamond-like carbon for medical stents and guidewires." *Diamond and Related Materials* 14, 1277-1288 (2005).
9. Marcon, et. al. "The head-disk interface roadmap to an areal density of 4 Tbit/in$^2$." *Advances in Tribology* 2013, 1-8 (2013).
10. Discher, D. E., Mooney, D. J. & Zandstra, P. W. "Growth Factors, Matrices, and Forces Combine and Control Stem Cells." *Science* 324, 1673-1677 (2009).
11. Spradling, A., Drummond-Barbosa, D. & Kai, T. "Stem cells find their niche." *Nature* 414, 98-104 (2001).
12. Murry, C. E. & Keller, G. "Differentiation of Embryonic Stem Cells to Clinically Relevant Populations: Lessons from Embryonic Development." *Cell* 132, 661-680 (2008).
13. Engler, A. J., Sen, S., Sweeney, H. L. & Discher, D. E. "Matrix Elasticity Directs Stem Cell Lineage Specification." *Cell* 126, 677-689 (2006).
14. Dalby, M. J. et al. "The control of human mesenchymal cell differentiation using nanoscale symmetry and disorder." *Nature Materials* 6, 997-1003 (2007).
15. Trappmann, B. et al. "Extracellular-matrix tethering regulates stem-cell fate." *Nature Materials* 11, 642-649 (2012).
16. Lee, H. et al. "Establishment of feeder-free culture system for human induced pluripotent stem cell on DAS nanocrystalline graphene." *Scientific Reports* 6, 20708 (2016).
17. Choi, W. J. et al. "Effects of substrate conductivity on cell morphogenesis and proliferation using tailored, atomic layer deposition-grown ZnO thin films." *Scientific Reports* 5, 9974 (2015).

All documents, patents, journal articles and other materials cited in the present application are incorporated herein by reference.

While the present disclosure has been disclosed with references to certain embodiments, numerous modification, alterations, and changes to the described embodiments are possible without departing from the sphere and scope of the present disclosure, as defined in the appended claims. Accordingly, it is intended that the present disclosure not be limited to the described embodiments, but that it has the full scope defined by the language of the following claims, and equivalents thereof.

What is claimed is:

1. A method of forming, an article comprising:
    a substrate; and
    a two-dimensional (2D) amorphous carbon film disposed on a surface of the substrate, wherein the 2D amorphous carbon film has a crystallinity in a range of 0.5≤(C)≤0.8 and is homogenous, the method comprising:
    decomposing a precursor gas to generate at least one decomposed species by photolytic decomposition; and
    forming the 2D amorphous carbon film from the at least one decomposed species on a surface of the substrate, wherein the precursor gas comprises a hydrocarbon as a precursor.

2. The method of claim 1, comprising:
    heating the substrate to a temperature of ≤500° C. prior to forming the 2D amorphous carbon film.

3. The method of claim 1, wherein the 2D amorphous carbon film is formed as a continuous film over substantially the entire substrate surface.

4. The method of claim 1, comprising:
    separating the 2D amorphous carbon film from the surface of the substrate to obtain a free-standing 2D amorphous carbon film.

5. The method of claim 1, comprising:
    transferring a free-standing 2D amorphous carbon film onto a surface of another substrate.

6. The method of claim 1, wherein the 2D amorphous carbon film has a transmittance equal to or greater than 98% at a wavelength of 550 nm to 650 nm.

* * * * *